(12) United States Patent
Tomer et al.

(10) Patent No.: US 10,956,437 B1
(45) Date of Patent: Mar. 23, 2021

(54) SYSTEMS AND METHODS FOR IMPLEMENTING SECURE DATABASE REQUESTS IN A ROLE-BASED APPLICATION ENVIRONMENT

(71) Applicant: TeleTracking Technologies, Inc., Pittsburgh, PA (US)

(72) Inventors: Anjali Tomer, Pittsburgh, PA (US);
Mark Wuslich, Pittsburgh, PA (US);
Deepak Bhurani, Pittsburgh, PA (US);
Jamie Slater, Pittsburgh, PA (US);
Kenneth Poling, Pittsburgh, PA (US);
Bhavya Sangars, Pittsburgh, PA (US);
Carol Cheng, Pittsburgh, PA (US);
Raghen Morrow, Pittsburgh, PA (US);
Twesha Mitra, Pittsburgh, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 0 days.

(21) Appl. No.: 16/166,630

(22) Filed: Oct. 22, 2018

Related U.S. Application Data

(60) Provisional application No. 62/575,439, filed on Oct. 21, 2017.

(51) Int. Cl.
| | |
|---|---|
| *G06Q 10/06* | (2012.01) |
| *G06F 16/25* | (2019.01) |
| *G16H 10/60* | (2018.01) |
| *H04L 29/08* | (2006.01) |
| *G06F 16/26* | (2019.01) |
| *G06F 16/2455* | (2019.01) |

(52) U.S. Cl.
CPC ........ *G06F 16/252* (2019.01); *G06F 16/2456* (2019.01); *G06F 16/26* (2019.01); *G16H 10/60* (2018.01); *H04L 67/327* (2013.01)

(58) Field of Classification Search
CPC .. G06F 16/24522; G06F 16/25; G06F 16/283; G06F 16/248; G06F 16/26; G06F 16/252; G06F 16/2456; G06F 16/2455; G16H 10/60; H04L 67/327
See application file for complete search history.

(56) References Cited

U.S. PATENT DOCUMENTS

| | | | |
|---|---|---|---|
| 7,325,007 B2 * | 1/2008 | Castro | G06F 16/2291 |
| 8,744,920 B2 * | 6/2014 | Aldomar | H04W 4/21 |
| | | | 705/26.1 |
| 9,158,828 B1 * | 10/2015 | Britton | G06F 16/27 |

(Continued)

*Primary Examiner* — Chirag R Patel
(74) *Attorney, Agent, or Firm* — Ference & Associates LLC

(57) ABSTRACT

The present disclosure relates to systems and methods for implementing secure database requests in a role-based application. In one example, the system may include at least one memory storing instructions and at least one processor configured to execute the instructions. The instructions may include instructions to receive, from a user device, a request to access data from a relational database; based on the request, extract the data from the relational database; perform one or more join commands on the data to generate an object in an object-oriented programming language having the joined data; convert the object to a data serialized format configured for use in a graphical user interface generator; and transmit the data serialized format to the user device.

20 Claims, 23 Drawing Sheets

(56) References Cited

U.S. PATENT DOCUMENTS

| | | | |
|---|---|---|---|
| 2011/0265188 A1* | 10/2011 | Ramaswamy | G06F 21/604 |
| | | | 726/28 |
| 2018/0069885 A1* | 3/2018 | Patterson | G06F 21/554 |
| 2018/0121843 A1* | 5/2018 | Connely, IV | G06Q 10/0633 |
| 2018/0314802 A1* | 11/2018 | Dreyer | G16H 40/20 |
| 2018/0358131 A1* | 12/2018 | Teodoro | G16H 50/30 |

* cited by examiner

SYSTEMS AND METHODS FOR IMPLEMENTING SECURE DATABASE REQUESTS IN A ROLE-BASED APPLICATION ENVIRONMENT

PRIORITY CLAIM

This application claims priority from U.S. Provisional Application No. 62/575,439, filed Oct. 21, 2017, which is hereby incorporated by reference in its entirety.

TECHNICAL FIELD

The present disclosure relates generally to the field of secure database requests. More specifically, and without limitation, this disclosure relates to systems and methods for implementing secure database requests in a role-based application environment.

BACKGROUND

The use of smartphones, tablets, and other user devices is increasing within the medical field. However, information in the medical field is subject to numerous privacy requirements, such as the Health Insurance Portability and Accountability Act in the United States, the Privacy Directive in the European Union, etc. Accordingly, pulling data about patients from databases must be performed in a secure manner in order to comply with such requirements.

In addition, varying members of a health organization may need to see different portions of data about patients and facilities such as operational data (e.g. bed data), aggregated data. Dashboards and physical displays may be used to manage and display operational data and aggregated data such as physician schedules and facility capacity metrics but may not be implemented at a mobile level. This may be on account of the needs of the roles of that member (e.g., executive data needs are different from nursing and doctor data needs) but may also be on account of privacy requirements (e.g., executives not permitted to see confidential patient-specific information). The lack of mobility and aggregation of the patient data and facility data causes delays in patient care and sub-optimal facility management.

SUMMARY

In view of the foregoing, embodiments of the present disclosure describe systems and methods for implementing secure database requests in a role-based application environment. The provided systems and methods may provide real-time visibility into patient and facility data. The provided systems may use geofencing, single sign-on (SSO), and/or other global security mechanism to provide a secure and private pull of patient data from one or more databases. Accordingly, the channel provided herein may be compliant with privacy laws and regulations as well as providing assurance to a patient that personal information is not being exposed.

In addition, the provided systems and methods may alter in functionality based on a role of the user. For example, the provided systems and methods allow for data requests to be automatically selected based on user input and on the role, and graphical user interfaces generated by the provided systems and methods may be based on the data requested and on the role. Accordingly, the display of the information may be customized to the needs of the role that the user occupies as well as preventing information from being pulled that may violate privacy laws and regulations.

In one embodiment, the present disclosure describes a system for implementing secure database requests in a role-based application. The system may comprise at least one memory storing instructions and at least one processor configured to execute the instructions. The instructions may comprise instructions to receive, from a user device, a request to access data from a relational database; based on the request, extract the data from the relational database; perform one or more join commands on the data to generate an object in an object-oriented programming language having the joined data; convert the object to a data serialized format configured for use in a graphical user interface generator; and transmit the data serialized format to the user device.

In another embodiment, the present disclosure describes a method for implementing secure database requests in a role-based application. The method may be executed by one or more processors. The method may comprise receiving, from a user device, a request to access data from a relational database; based on the request, extracting the data from the relational database; performing one or more join commands on the data to generate an object in an object-oriented programming language having the joined data; converting the object to a data serialized format configured for use in a graphical user interface generator; and transmitting the data serialized format to the user device.

In some embodiments, the present disclose describes non-transitory, computer-readable media for causing one or more processors to execute methods consistent with the present disclosure.

In yet another embodiment, a non-transitory, computer-readable medium may store instructions for implementing secure database requests in a role-based application. The instructions may cause one or more processors to generate a request for data from a relational database; transmit the request to a remote device; receive, in response to the request, a data serialized format including the data; and generate a graphical user interface including visual representations of the data in the data serialized format. The data requested may be selected based on user input and based on a role of the user. Moreover, the generated graphical user interface may be selected from a plurality of graphical user interfaces based on the requested data and based on the role.

In an additional embodiment, the present disclosure describes a method for implementing secure database requests in a role-based application. The method may be executed by one or more processors. The method may comprise generating a request for data from a relational database; transmitting the request to a remote device; receiving, in response to the request, a data serialized format including the data; and generating a graphical user interface including visual representations of the data in the data serialized format. The data requested may be selected based on user input and based on a role of the user. Moreover, the generated graphical user interface may be selected from a plurality of graphical user interfaces based on the requested data and based on the role.

It is to be understood that the foregoing general description and the following detailed description are example and explanatory only, and are not restrictive of the disclosed embodiments.

BRIEF DESCRIPTION OF THE DRAWINGS

The accompanying drawings, which comprise a part of this specification, illustrate several embodiments and, together with the description, serve to explain the principles disclosed herein. In the drawings.

DETAILED DESCRIPTION

Figure 1:
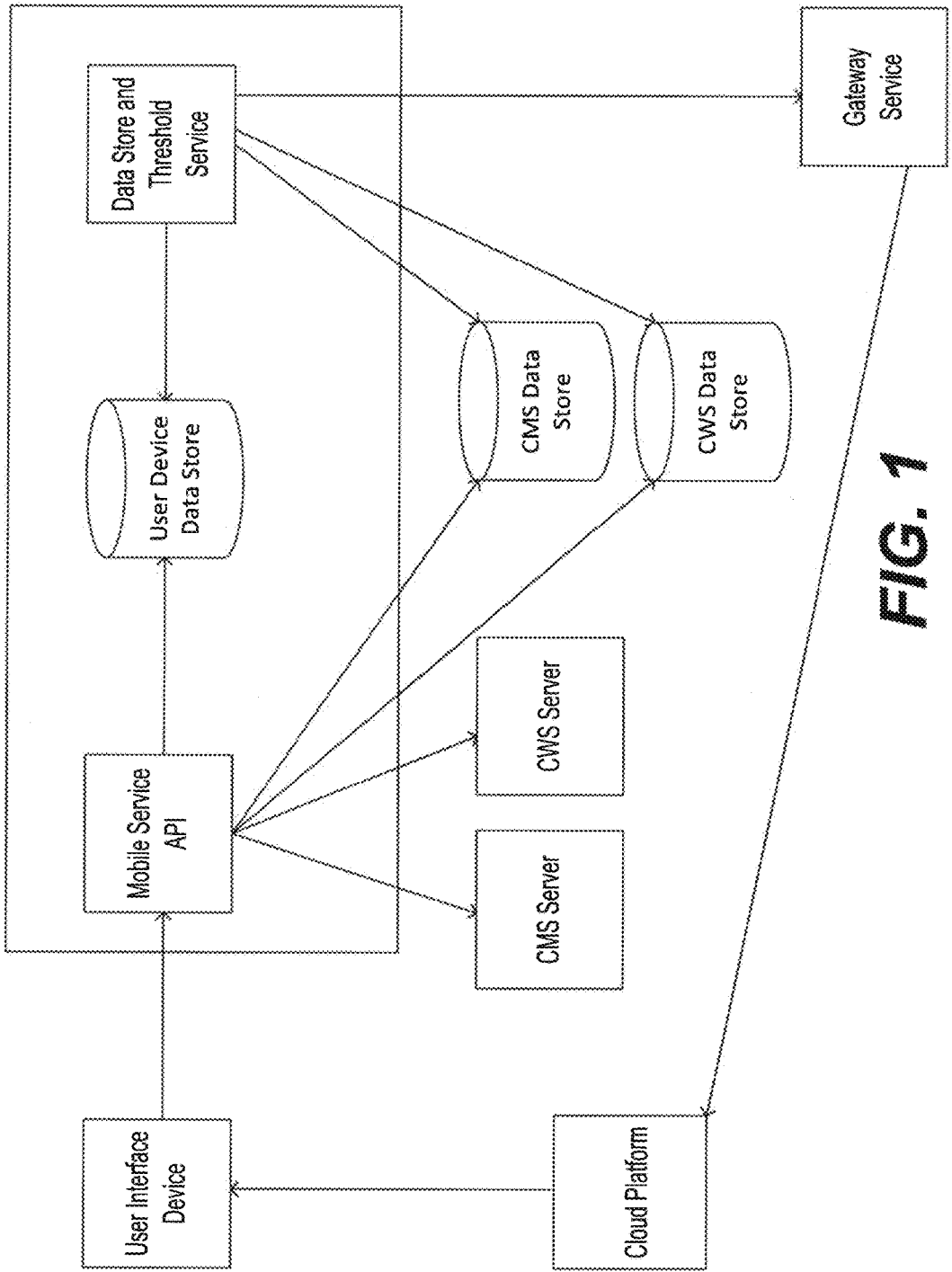
FIG. 1 is a block diagram of a system for implementing secure database pulls in a role-based application environment, according to an example embodiment of the present disclosure.

The disclosed embodiments relate to systems and methods for generating and fulling secure database pulls in a role-based application environment. Embodiments of the present disclosure may be implemented using a general-purpose computer. Alternatively, a special-purpose computer may be built according to embodiments of the present disclosure using suitable logic elements.

Advantageously, disclosed embodiments may provide for secure and confidential pulls from medical databases. Accordingly, the database pulls may be adjusted based on user input and on user roles to ensure the most useful data is pulled and that the pulls are compliant with privacy concerns.

According to an aspect of the present disclosure, one or more servers or other computing devices may store data relating to patients in a hospital or other medical campus or network. For example, data may be stored and indexed based on patient. In addition, data may be stored and indexed by beds, including vacant (or available) beds.

In some embodiments, the servers or other computing devices may aggregate patient-specific and/or bed-specific data into one or more statistics. The servers or other computing devices may communicate with each other or with patient beds using a threshold service, a web service, a database. For example, a total number of available beds, a total number of occupied beds, a total number of patients, or the like may be calculated. Additional statistics may be derived from various aggregations. For example, the servers may calculate a ratio or percentage of available beds, a ratio or percentage of patients awaiting care to patients receiving care, or the like. The statistics may also be aggregated based on locations (e.g., average wait time by campus, percentage of available beds by building, percentage of patients by category such as radiology or geriatrics, or the like), may be aggregated based on statuses (e.g., percentage of vacant beds, percentage of vacant beds that are clean, or the like).

In some embodiments, the data may be encrypted. Alternatively, the aggregated statistics may be stored in an unencrypted format to increase speed of access without violating privacy concerns.

The servers may receive, from a user device, a request to access data from a relational database. The relational database may store the data in rows and columns and may be positioned locally. For example, the user may comprise a caregiver (such as a doctor, nurse, surgeon, or the like) and may send the request using a user interface device such as a smartphone, tablet, laptop, or the like. The request may be sent over one or more computer networks, such as the Internet, a local area network (LAN), or the like, and may be sent using WiFi, 4G, Ethernet, or the like. In some embodiments, to retain security, the request may be sent over a private network (such as a LAN) and/or may be encrypted (e.g., using an Advanced Encryption Standard (AES)). In embodiments where the request is encrypted, the servers may decrypt the request using a private key. Similarly, in embodiments where any of the requested data is encrypted, the servers may decrypt during the extraction of the data.

The relational database may include patient-specific and/or bed-specific data and/or may include aggregated data described above. In some embodiments, the aggregated data may have been converted from a relational database to an object in an object-oriented programming language. For example, the servers may perform one or more join commands on the data to generate an object in an object-oriented programming language having the joined data. The join commands may be in an appropriate relational database language such as SQL.

Based on the request, the servers may extract the data from the relational database. For example, the servers may generate one or more commands in an appropriate relational database language such as SQL to extract the data. In embodiments where the aggregated data is stored as one or more objects, the servers may extract the aggregated data using an index or other matching technique to match the appropriate object(s) to the request. In some embodiments, mobile servers may access a mobile store, the mobile store having a plurality of mobile applications that may store data. The mobile servers may transmit a query to the mobile store to aggregate the data from the mobile applications. The mobile servers may submit queries to the mobile store regularly (e.g. at two-minute intervals) in order to maintain a real-time access to the data. In some embodiments, the servers may perform one or more join commands on at least part of the extracted data (e.g., a part that is not already stored in an object) to generate an object in an object-oriented programming language having the joined data.

Once the extracted data is stored as one or more objects, the servers may convert the object to a data serialized format configured for use in a graphical user interface generator. For example, the objects may be converted to a JavaScript Object Notation (JSON) file, an Extensible Markup Language (XML) file, or the like. Such files may allow for compatibility with web-based application programming interfaces (APIs). Accordingly, the request received from the user device may comprise an API pull of a data serialized format.

In alternate embodiments, the servers may store the patient-specific and/or bed-specific data along with the aggregated data in a NoSQL database, such as MongoDB. In such embodiments, the request received from the user device may comprise a MongoDB pull, and the servers may directly extract the data serialized format from the MongoDB database based on the pull.

In embodiments where aggregated data is requested and pulled, the request and/or the data serialized format may be unencrypted. This increases speed of access without violating privacy concerns. Alternatively, the request and/or the data serialized format may be encrypted.

In embodiments where patient-specific data is requested and pulled, at least the portion of the request corresponding to the patient-specific data and/or at least the portion of the data serialized format corresponding to the patient-specific data may be encrypted. This may retain the privacy of medical data while allowing for any aggregated (or other non-private) data to remain unencrypted.

The data serialized format may be configured for use in a graphical user interface generator. For example, the graphical user interface generator may be configured to select one of a plurality of graphical user interfaces customized based on a role of the user.

One example of a customized graphical user interface is an interface for an executive. Such an interface may include a census screen displaying patient capacity for each campus in a medical system. The interface may further include a campus-specific census screen displaying statistics such as the total number of waiting patients, the longest wait of a patient, the average wait of a patient, the average turn time for beds, or the like. The interface may also include a campus-specific breakdown screen which may show similar statistics for each category (e.g., emergency room (ER), radiology, or the like).

A second example of a customized graphical user interface is an interface for a nurse manager (or a "charge nurse"). Such an interface may include a census screen displaying bed status for each unit (e.g., building, wing of a building, or the like) in a medical system. The interface may further include a unit-specific breakdown screen displaying details on each bed within the unit. The interface may also include a census screen displaying bed status, intake statistics, discharge statistics, and the like for each campus in the medical system. This information may be stored in mobile applications as discussed above, where the mobile applications may be directly accessed via a query to the mobile store. The interface may also include a campus-specific breakdown screen which may show statistics such as average placement time, average discharge time, number of incoming patients, bed requests, bed assignments, discharges pending, and the like. To further assist a nurse manager, the interface may include a campus-specific breakdown screen showing statistics for each category (e.g., emergency room (ER), radiology, or the like) in the campus. Accordingly, the interfaces for the nurse manager many include increasing detailed breakdowns as compared with the executive interfaces.

A third example of a customized graphical user interface is an interface for a nurse. The interfaces for a nurse may be similar to those for a nurse manager but may be limited to the subset of patients that a specific nurse is serving. In addition, the interfaces may include order statuses and lab statuses for specific patients, as well as progress charts for nurses to track the progress of their specific patients.

A fourth example of a customized graphical user interface is an interface for a patient flow manager. The interfaces for a patient flow manager may be similar to those for a nurse manager but with additional staffing details. For example, each campus, each unit, and/or each category may include statistics about staffing levels in each, allowing a patient flow manager to see if staff should be shifted in accordance with demand. In addition, the per-bed interfaces may display names of employees that are assigned to staff each bed and/or if a bed is awaiting a staffing assignment.

A fifth example of a customized graphical user interface is an interface for a transporter. The interfaces for a transporter may be similar to those for a nurse but include progress tracking for transporters rather than nurses. In addition, statistics regarding average time to transport, delayed patient transports, and the like may also be displayed.

A sixth example of a customized graphical user interface is an interface for a surgeon. The interfaces for a surgeon may be similar to those for a nurse but include progress tracking pre-op and post-op procedures rather than progress tracking for nurses. In addition, statistics regarding on-time surgeries, delays, average time of delay, or the like may also be displayed. These statistics may be updated and accessed via mobile applications on a mobile store, as discussed above. In such an example, a practitioner's schedule may be updated based on on-time surgeries, delays, average time of delay, or the like. This data may be entered into mobile applications and may be accessed via a query from the mobile server to the mobile store to receive the aggregated data.

A seventh example of a customized graphical user interface is an interface for a community physician. The interfaces for a community physician may be limited to that physician's patients. In addition, statistics regarding admit status and/or transport status of patients for which the physician has requested admission and/or transport may be displayed.

Any of the above interfaces may further include warnings when any statistics exceeds thresholds. The threshold may be determined by the system or in accordance with one or more settings selected by the user. For example, the executive may select a setting to see a message whenever the average wait exceeds 30 minutes, or to see a message whenever the patient capacity is within 5% of the capacity of a campus, etc.

In some embodiments, the servers may further monitor the aggregated data and transmit a notification to the user when a threshold is reached. The threshold may be determined by the system or in accordance with one or more settings selected by the user. For example, when the capacity of a campus exceeds a threshold, the servers may push a notification to one or more executives. By way of further example, when the average bed turn exceeds two hours, the servers may push a notification to one or more nurse managers.

The servers may transmit the data serialized format to the user device. For example, the servers may transmit the data serialized format over one or more computer networks, such as the Internet, a local area network (LAN), or the like, and may be sent using WiFi, 4G, Ethernet, or the like. In some embodiments, to retain security, the data serialized format may be sent over a private network (such as a LAN) and/or may be encrypted (e.g., using an Advanced Encryption Standard (AES)). In embodiments where the data serialized format is encrypted, the user interface device may decrypt the data serialized format, e.g., using a private key.

In a related embodiment, a user may generate a request for data from a relational database. For example, the user may generate the request using a user interface device, e.g., device 1600 of FIG. 23. The request may be generated manually (e.g., by the user) and/or automatically (e.g., in response to the navigation to a particular screen or portion of an application by the user). In an alternative embodiment, the request may comprise a NoSQL request, such as a MongoDB request.

The requested data may be based on user input. For example, as explained above, the input may directly request particular data or may be generated automatically based on user navigation within an application (e.g., a particular interface may require particular data). The requested data may be further based on a role of the user. For example, the request may only include aggregated data if the user is an executive. In another example, the request may include requests for patient-specific identifiers such as names if the user is a nurse, a surgeon, or a community physician.

The user interface device may transmit the request to a remote device. For example, the user interface device may transmit the request over one or more computer networks, such as the Internet, a local area network (LAN), or the like, and may be sent using WiFi, 4G, Ethernet, or the like. In some embodiments, to retain security, the request may be sent over a private network (such as a LAN) and/or may be encrypted (e.g., using an Advanced Encryption Standard (AES)). In embodiments where the request is encrypted, the servers may decrypt the request, e.g., using a private key.

The user interface device may receive, in response to the request, a data serialized format including the data. For example, the data serialized format may comprise a JavaScript Object Notation (JSON) file, an Extensible Markup Language (XML) file, or the like.

The user interface device may generate a graphical user interface including visual representations of the data in the data serialized format. For example, the customized graphical interfaces discussed above may be used to display the data. Graphical representations may include pie charts, bar graphs, and other visual representations of the received data. The graphical interfaces may also include text and numbers displaying the received data.

In FIG. 1, there is shown a block diagram of a system for implementing secure database pulls in a role-based application environment. As depicted in FIG. 1, a user interface device associated with a user having a role may request information using a mobile service API. The mobile service API may receive unencrypted and/or encrypted requests. In some embodiments, the mobile service API may require connection to a private network (and/or to a virtual private network (VPN)) for requests to be received. This may, for example, allow for aggregated data and requests to remain unencrypted without significant risk of interception.

As further depicted in FIG. 1, the mobile server API may authenticate the user on a content management system (CMS) server and/or a cloud web service (CWS) server. Such authentication may verify that the user has the credentials to view requested data. Additionally, the CMS server and/or CWS sever may confirm that a role of the user is permitted to view the requested data. For example, a request from an executive to view patient-specific data may be denied by the CMS server and/or CWS server.

As depicted in FIG. 1, data store and threshold service may pull data from the CMS data store and/or the CWS data store and aggregate the data for storage in the user device data store. By executing aggregation on a period basis rather than on an on-demand basis, the system may reduce resource bottlenecks. In addition, the system may leave the aggregated data in user device data store unencrypted for fast access while keeping patient-specific data in the CMS data store and/or CWS data store encrypted to comply with privacy laws and regulations.

The data store and threshold service may also implement the monitoring and notification discussed above. For example, while aggregating data, the data store and threshold service may check the aggregated data against any system-specific thresholds and any stored user-specific thresholds and generate any notifications for delivery through the gateway service and cloud platform. The cloud platform may operate over a public or private network. In some embodiments, then, the notification may be encrypted. In other embodiments, the notification may remain unencrypted because it only includes aggregated data.

Figure 2:
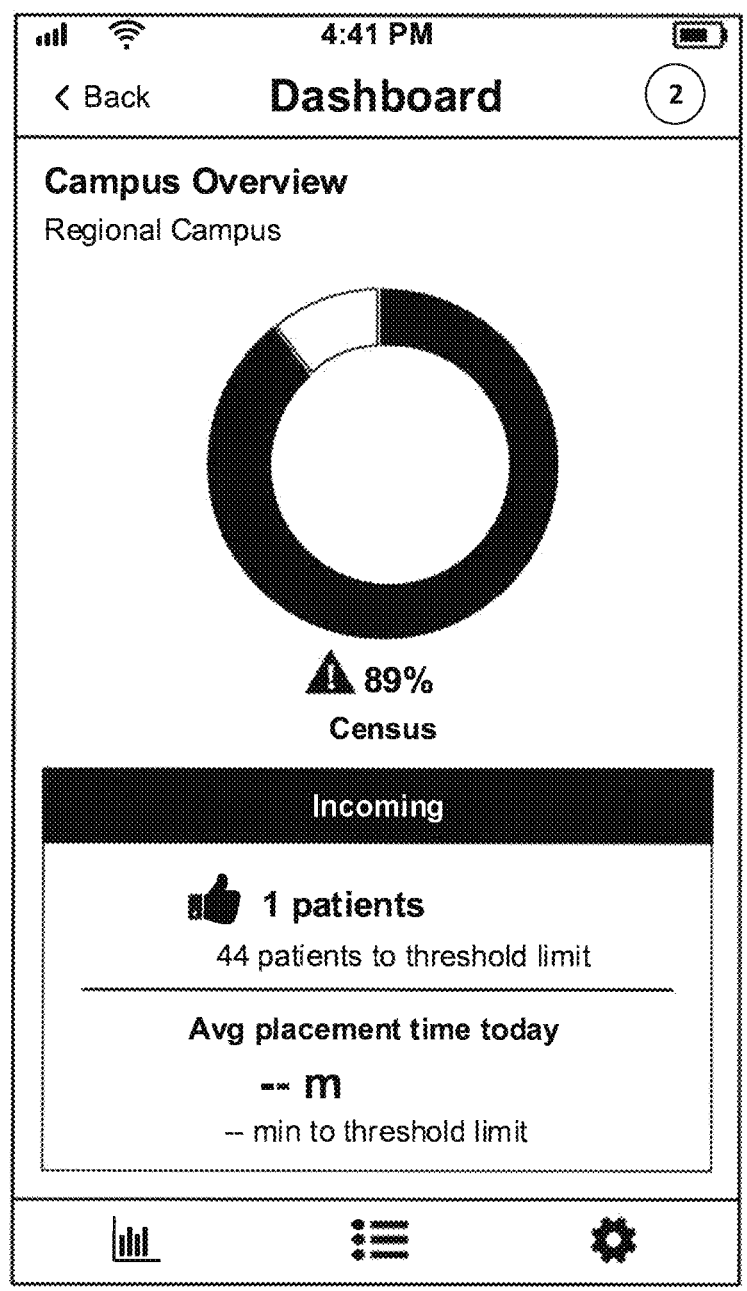
FIG. 2 is an example graphical user interface for visualizing data from a secure database pull in a role-based application, according to an example embodiment of the present disclosure.

FIG. 2 depicts a graphical user interface 200 for visualizing data from a secure database pull in a role-based application, for example in a patient flow management role. Interface 200 may be generated for display on a screen of a user interface device (e.g., screen 1601 of FIG. 23). In the example of FIG. 2, a census screen for an executive, as described above, is depicted.

Figure 3:
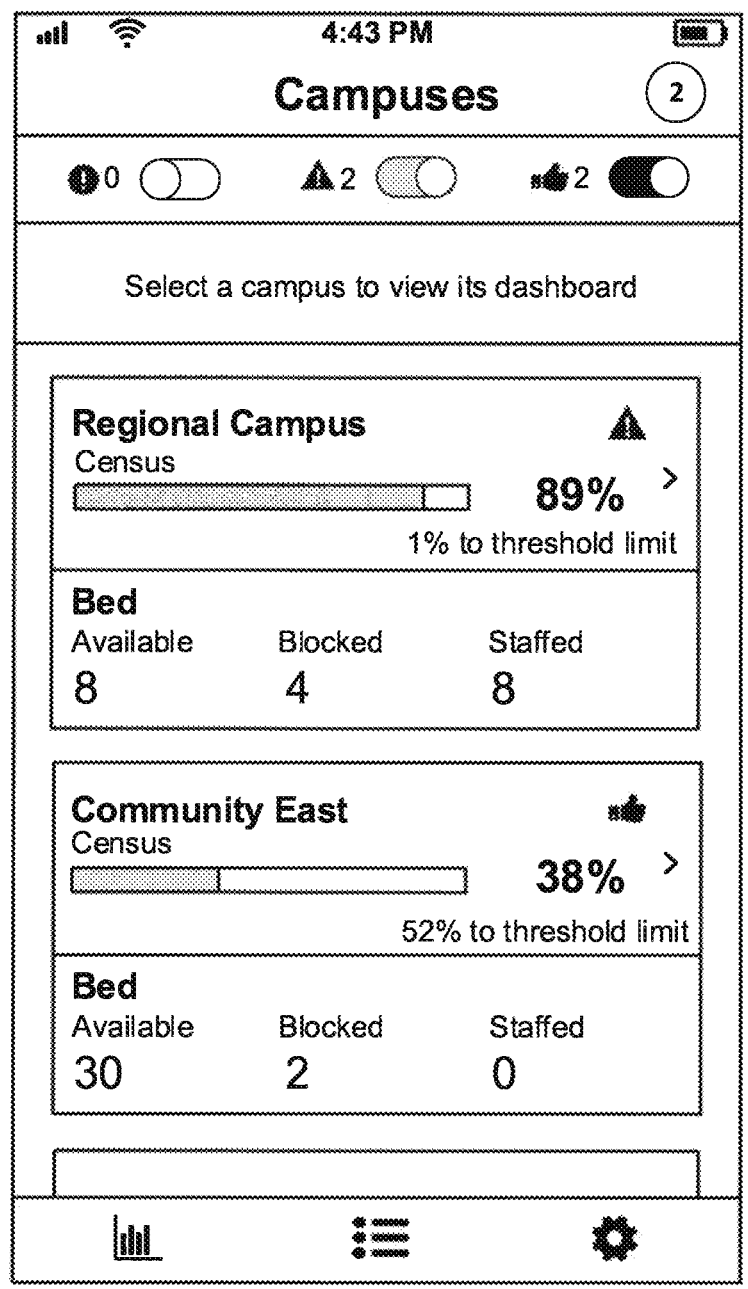
FIG. 3 is a second example graphical user interface for visualizing data from a secure database pull in a role-based application, according to an example embodiment of the present disclosure.

FIG. 3 depicts a graphical user interface 300 for visualizing data from a secure database pull in a role-based application, for example in a patient flow management role. Interface 300 may be generated for display on a screen of a user interface device (e.g., screen 1601 of FIG. 23). As depicted in FIG. 3, an executive may select which campus-specific census screen to view.

Figure 4:
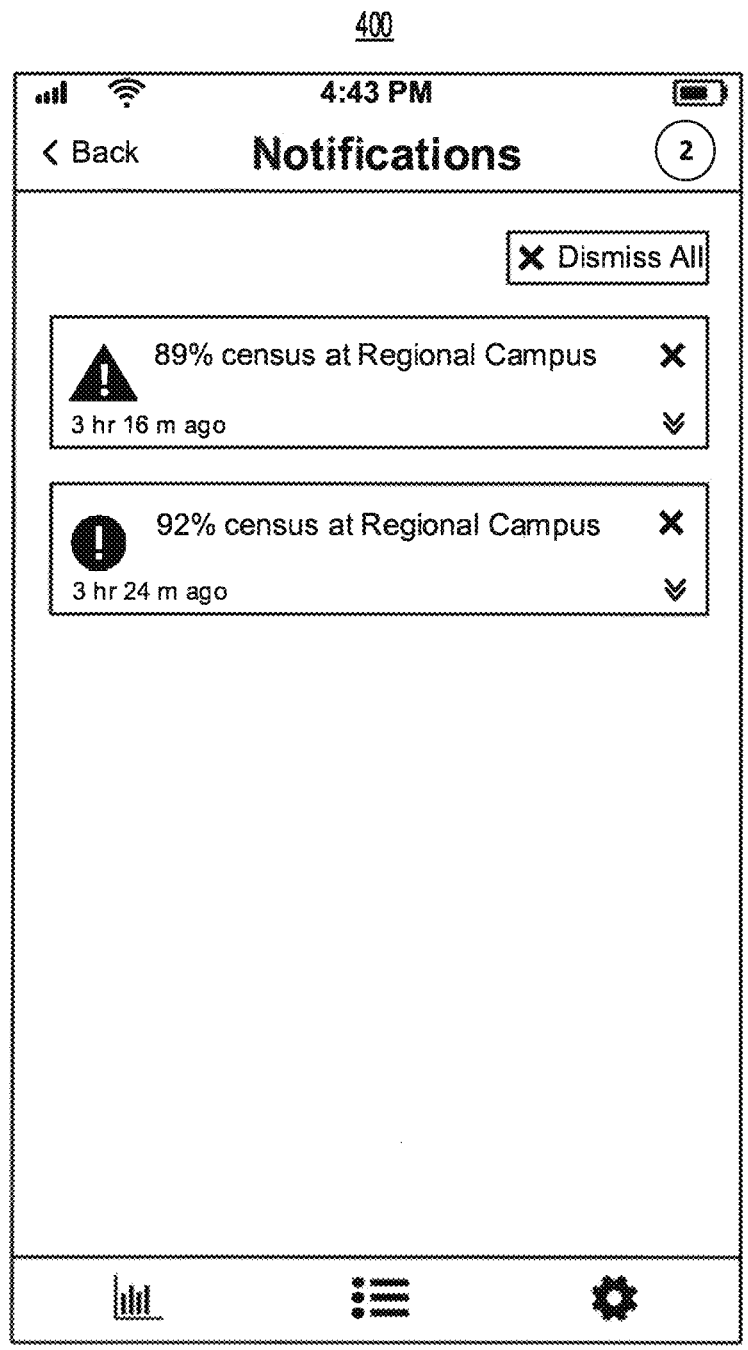
FIG. 4 is a third example graphical user interface for visualizing data from a secure database pull in a role-based application, according to an example embodiment of the present disclosure.

FIG. 4 depicts a graphical user interface 400 for visualizing data from a secure database pull in a role-based application, for example in a patient flow management role. Interface 400 may be generated for display on a screen of a user interface device (e.g., screen 1601 of FIG. 23). In the example of FIG. 4, a notifications screen in displayed. For example, the notifications screen may be for a nurse manager or a patient flow manager and may include both capacity alerts as well as alerts regarding long wait times for specific patients. A notifications screen for an executive may not include patient-specific alerts.

Figure 5:
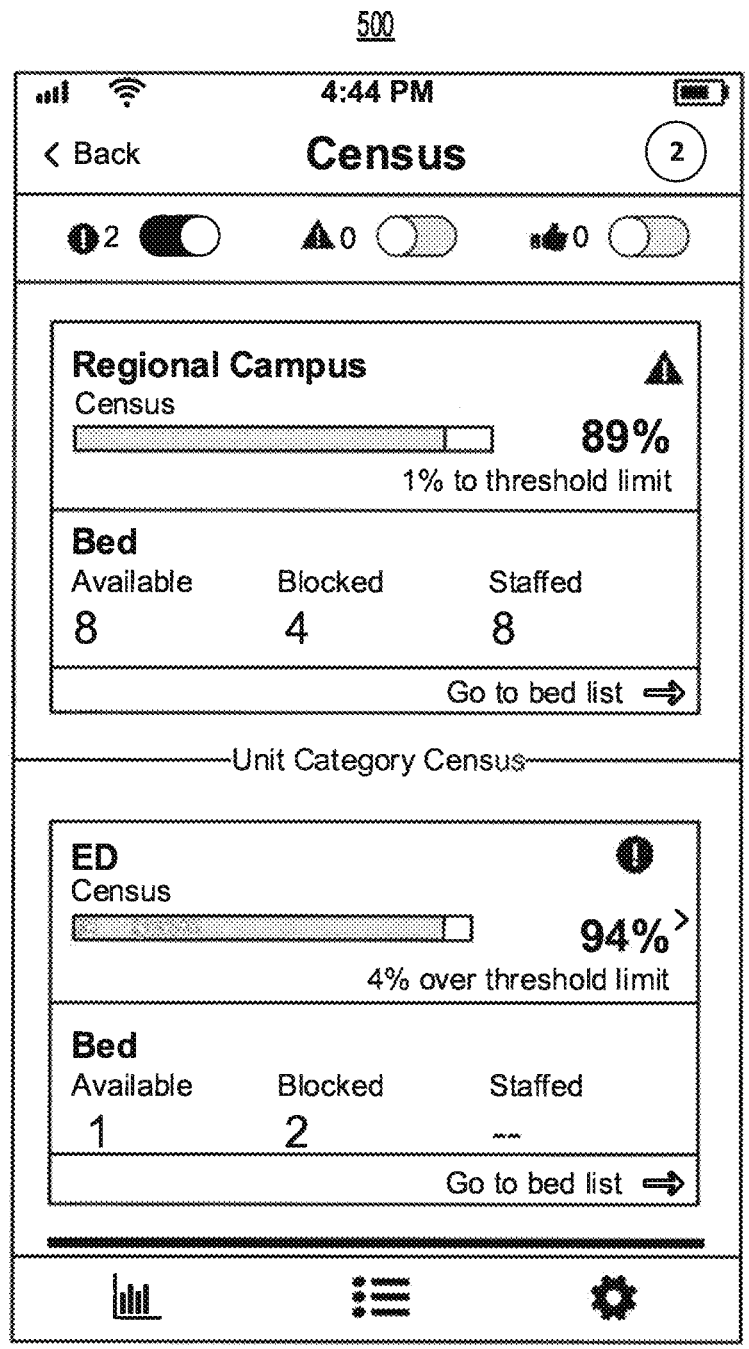
FIG. 5 is a fourth example graphical user interface for visualizing data from a secure database pull in a role-based application, according to an example embodiment of the present disclosure.

FIG. 5 depicts a graphical user interface 500 for visualizing data from a secure database pull in a role-based application, for example in a patient flow management role. Interface 500 may be generated for display on a screen of a user interface device (e.g., screen 1601 of FIG. 23). In the example of FIG. 5, a campus-specific census screen for an executive, as described above, is depicted.

Figure 6:
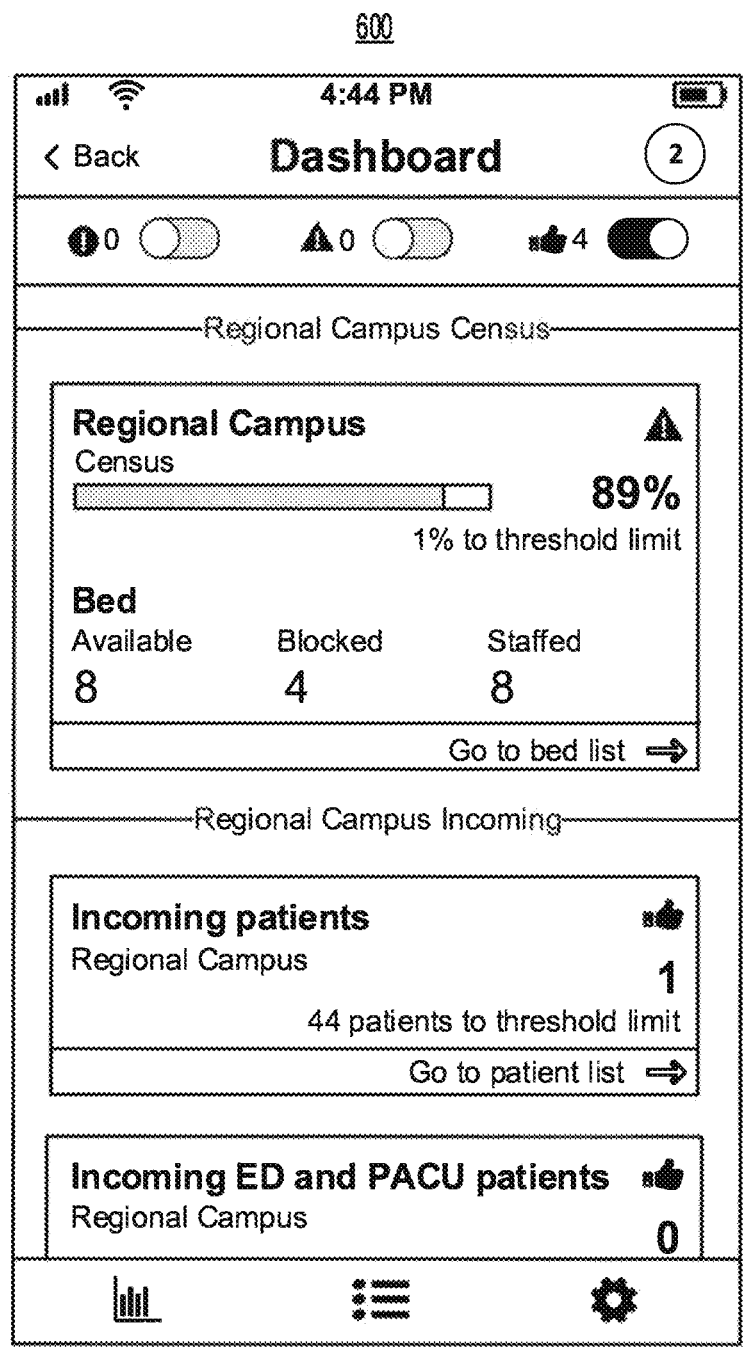
FIG. 6 is a fifth example graphical user interface for visualizing data from a secure database pull in a role-based application, according to an example embodiment of the present disclosure.

FIG. 6 depicts a graphical user interface 600 for visualizing data from a secure database pull in a role-based application, for example in a patient flow management role. Interface 600 may be generated for display on a screen of a user interface device (e.g., screen 1601 of FIG. 23). In the example of FIG. 6, a campus-specific census screen for a nurse manager, as described above, is depicted. As can be seen, the campus-specific census screen includes more details, particularly details about bed status, than the campus-specific census screen for an executive as depicted in FIG. 5.

Figure 7:
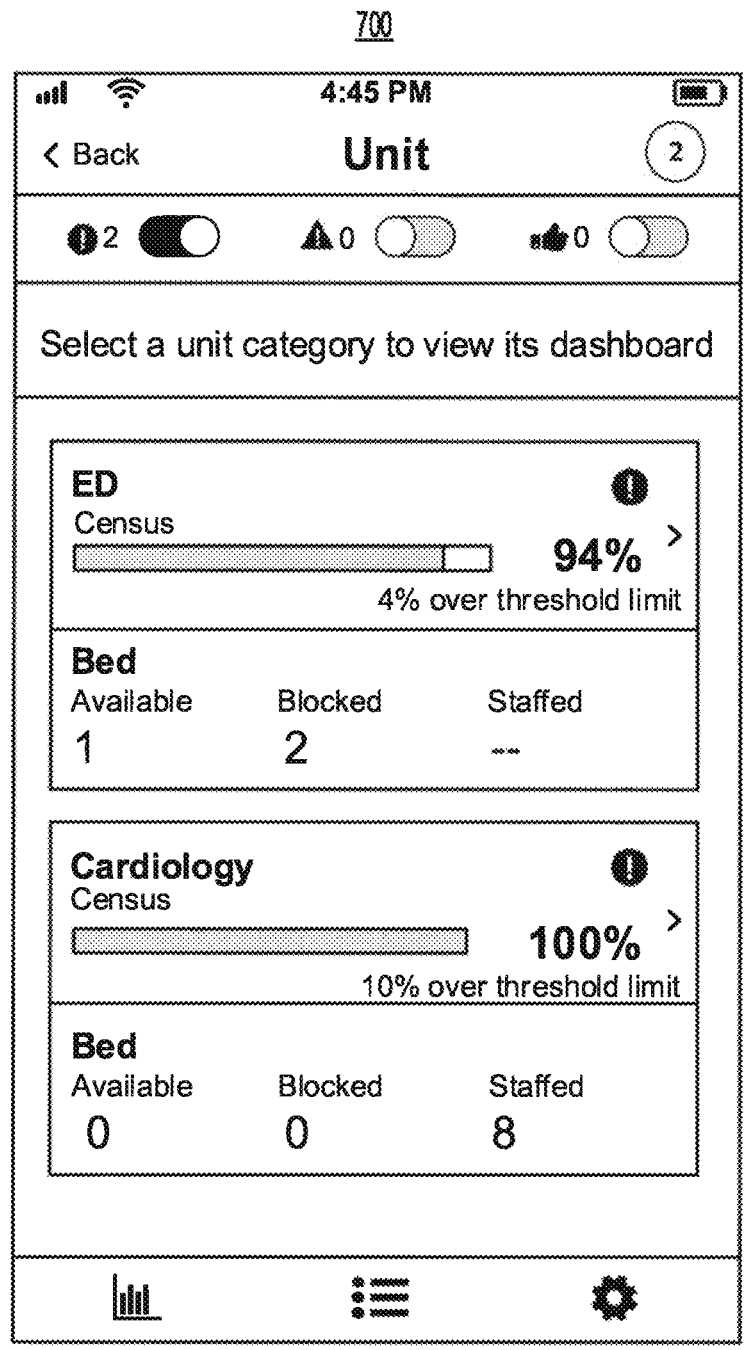
FIG. 7 is a sixth example graphical user interface for visualizing data from a secure database pull in a role-based application, according to an example embodiment of the present disclosure.

FIG. 7 depicts a graphical user interface 700 for visualizing data from a secure database pull in a role-based application, for example in a patient flow management role. Interface 700 may be generated for display on a screen of a user interface device (e.g., screen 1601 of FIG. 23). In the example of FIG. 7, a category-specific census screen for a nurse manager, as described above, is depicted.

Figure 8:
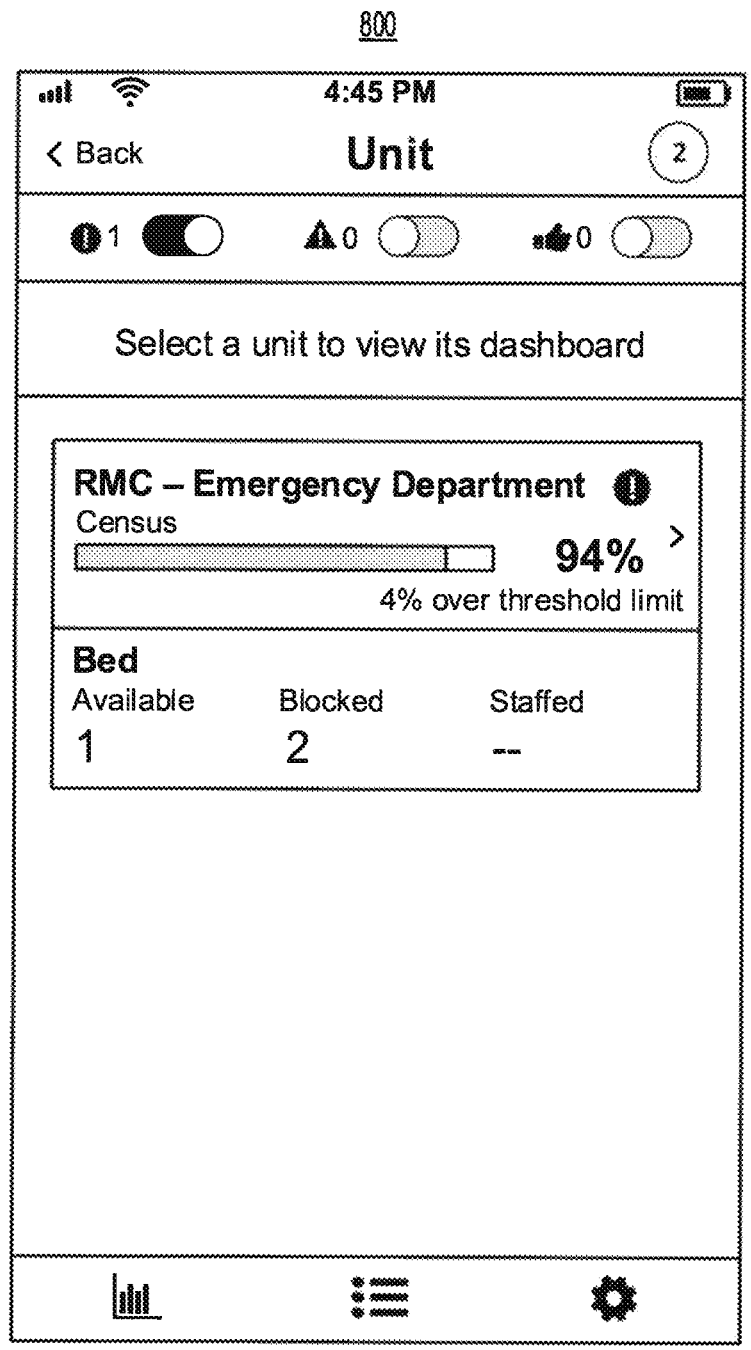
FIG. 8 is a seventh example graphical user interface for visualizing data from a secure database pull in a role-based application, according to an example embodiment of the present disclosure.

FIG. 8 depicts a graphical user interface 800 for visualizing data from a secure database pull in a role-based application, for example in a patient flow management role. Interface 800 may be generated for display on a screen of a user interface device (e.g., screen 1601 of FIG. 23). In the example of FIG. 8, a unit-specific census screen for a patient flow manager, as described above, is depicted.

Figure 9:
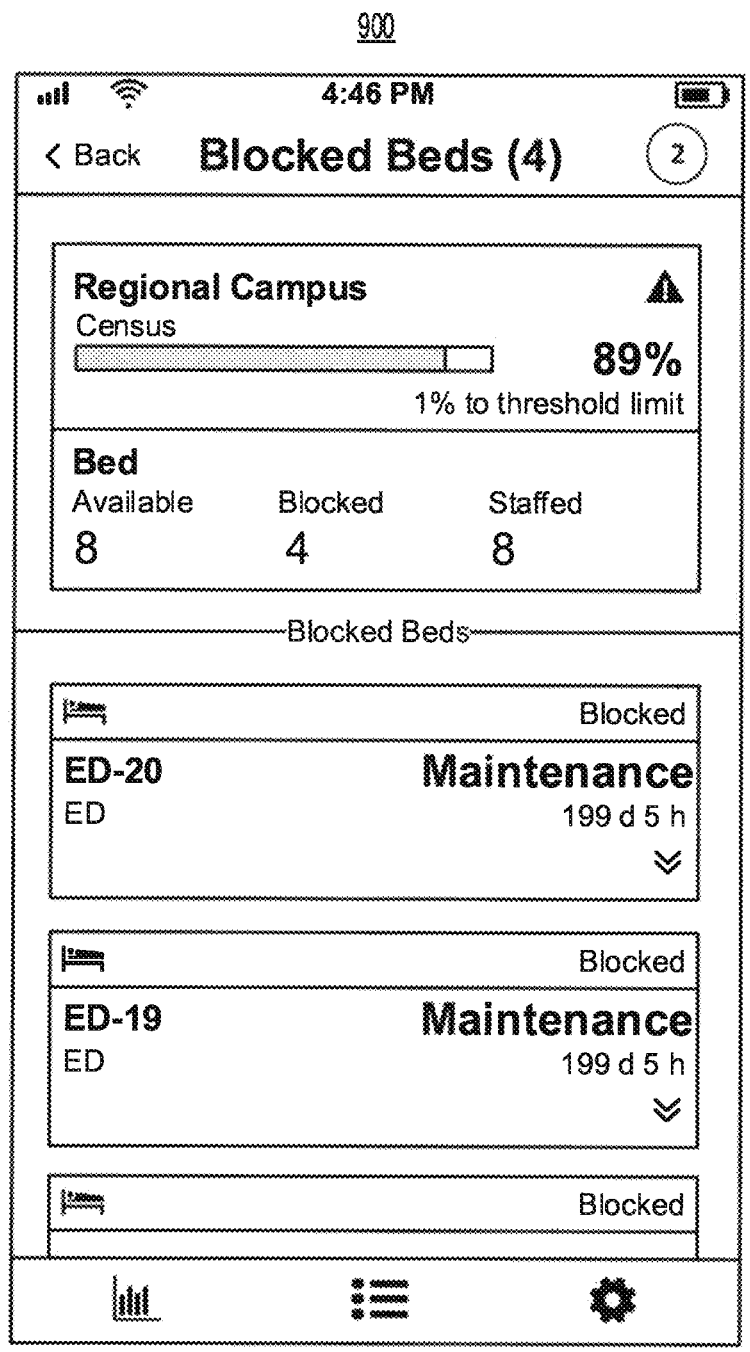
FIG. 9 is an eighth example graphical user interface for visualizing data from a secure database pull in a role-based application, according to an example embodiment of the present disclosure.

FIG. 9 depicts a graphical user interface 900 for visualizing data from a secure database pull in a role-based application, for example in a patient flow management role. Interface 900 may be generated for display on a screen of a user interface device (e.g., screen 1601 of FIG. 23). In the example of FIG. 9, a unit-specific breakdown screen for a patient flow manager, as described above, is depicted.

Figure 10:
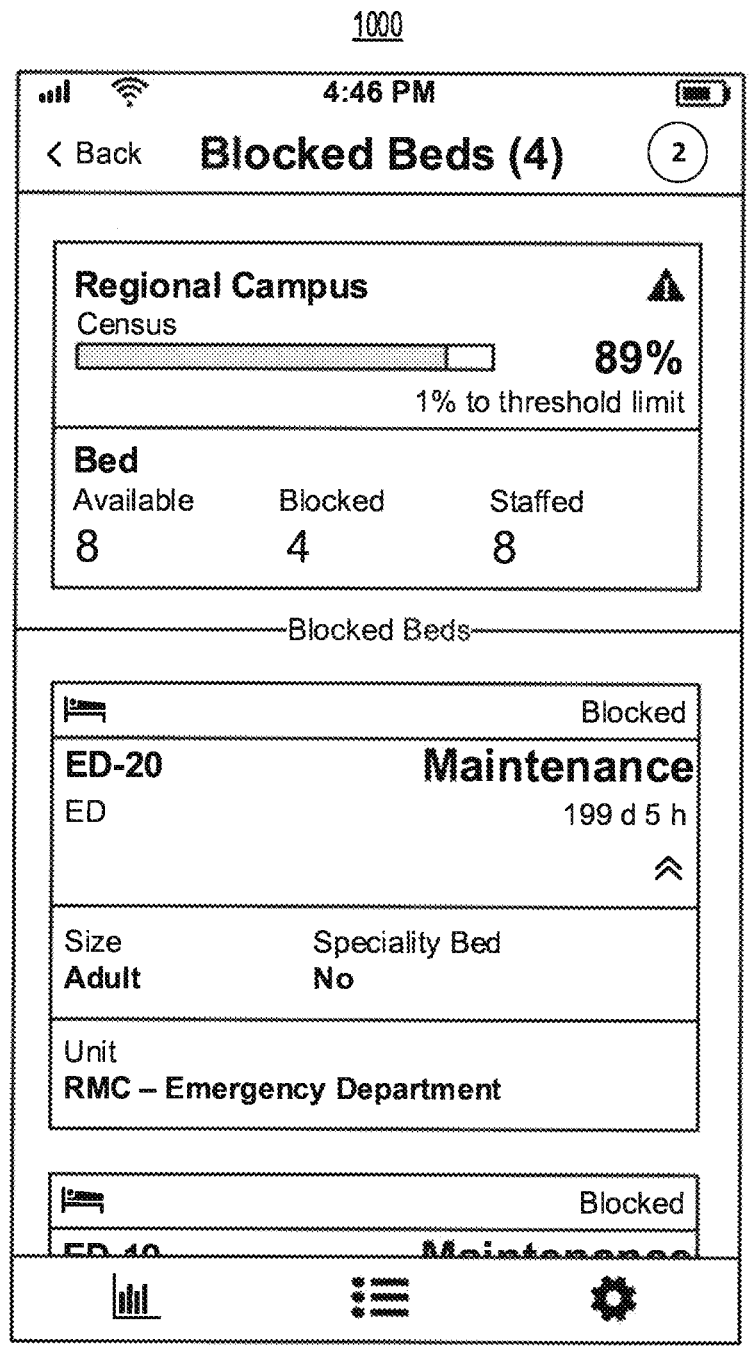
FIG. 10 is a ninth example graphical user interface for visualizing data from a secure database pull in a role-based application, according to an example embodiment of the present disclosure.

FIG. 10 depicts a graphical user interface 1000 for visualizing data from a secure database pull in a role-based application, for example in a patient flow management role. Interface 1000 may be generated for display on a screen of a user interface device (e.g., screen 1601 of FIG. 23). In the example of FIG. 10, a patient flow manager is permitted to access additional details on each bed from the unit-specific breakdown screen, e.g., by opening a drop-down menu. Similar details may be access from a list of beds awaiting cleaning or the like as well as from a category-specific breakdown screen.

Figure 11:
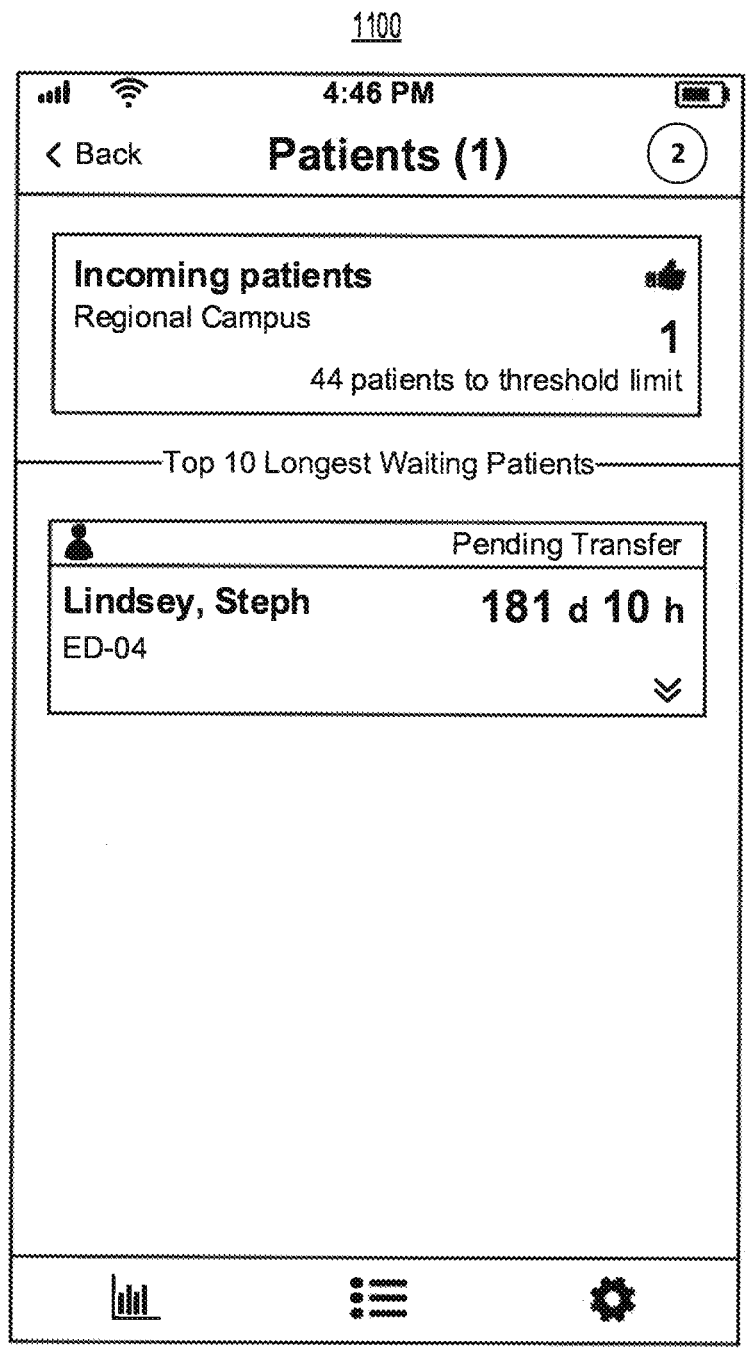
FIG. 11 is a tenth example graphical user interface for visualizing data from a secure database pull in a role-based application, according to an example embodiment of the present disclosure.

FIG. 11 depicts a graphical user interface 1100 for visualizing data from a secure database pull in a role-based application, for example in a patient flow management role. Interface 1100 may be generated for display on a screen of a user interface device (e.g., screen 1601 of FIG. 23). In the example of FIG. 11, a list of ten longest waiting patients may be provided to a patient flow manager. Such lists may also be used to see which campuses have most or least capacity, which units or categories have longest wait times, or the like.

Figure 12:
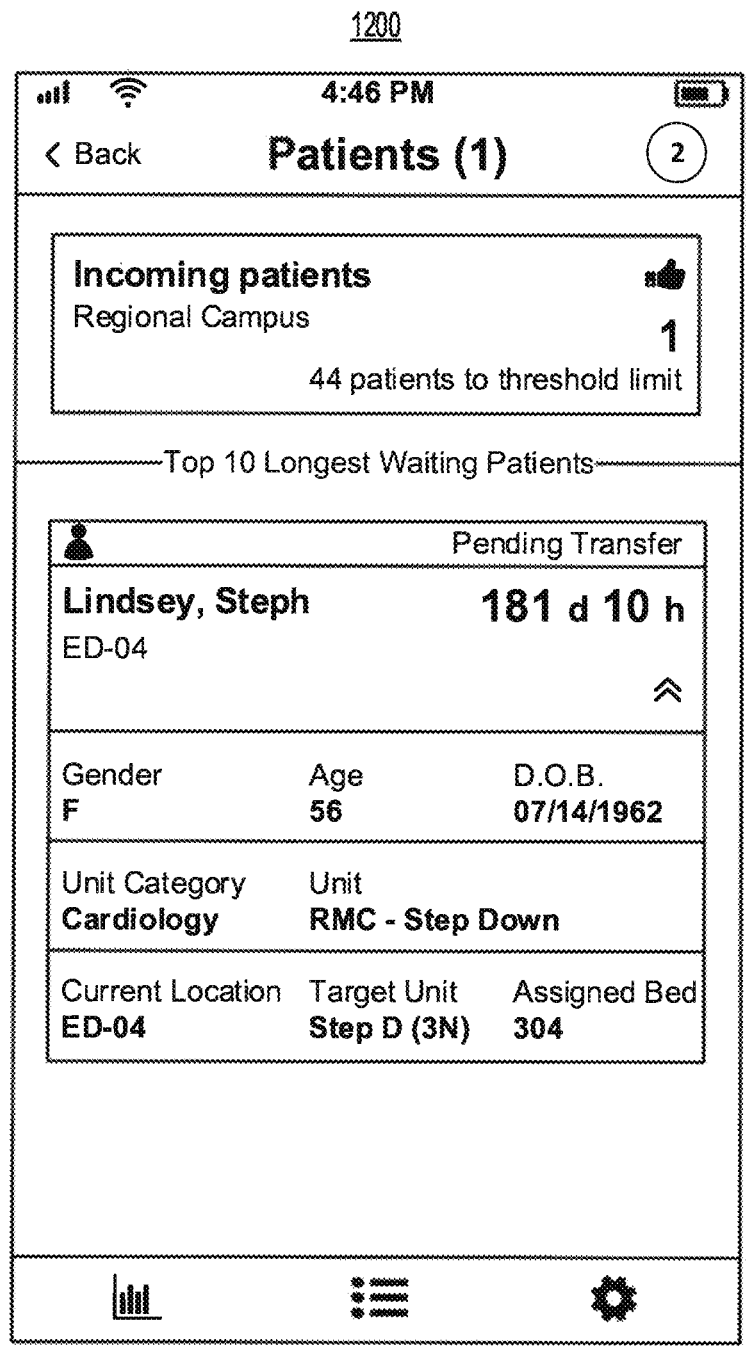
FIG. 12 is an eleventh example graphical user interface for visualizing data from a secure database pull in a role-based application, according to an example embodiment of the present disclosure.

FIG. 12 depicts a graphical user interface 1200 for visualizing data from a secure database pull in a role-based application, for example in a patient flow management role. Interface 1200 may be generated for display on a screen of a user interface device (e.g., screen 1601 of FIG. 23). In the example of FIG. 12, a patient flow manager is permitted to access additional details on each patient from the list of longest waiting patients, e.g., by opening a drop-down menu. Similar details may be accessed from unit-specific or category-specific lists of patients or the like.

Figure 13:
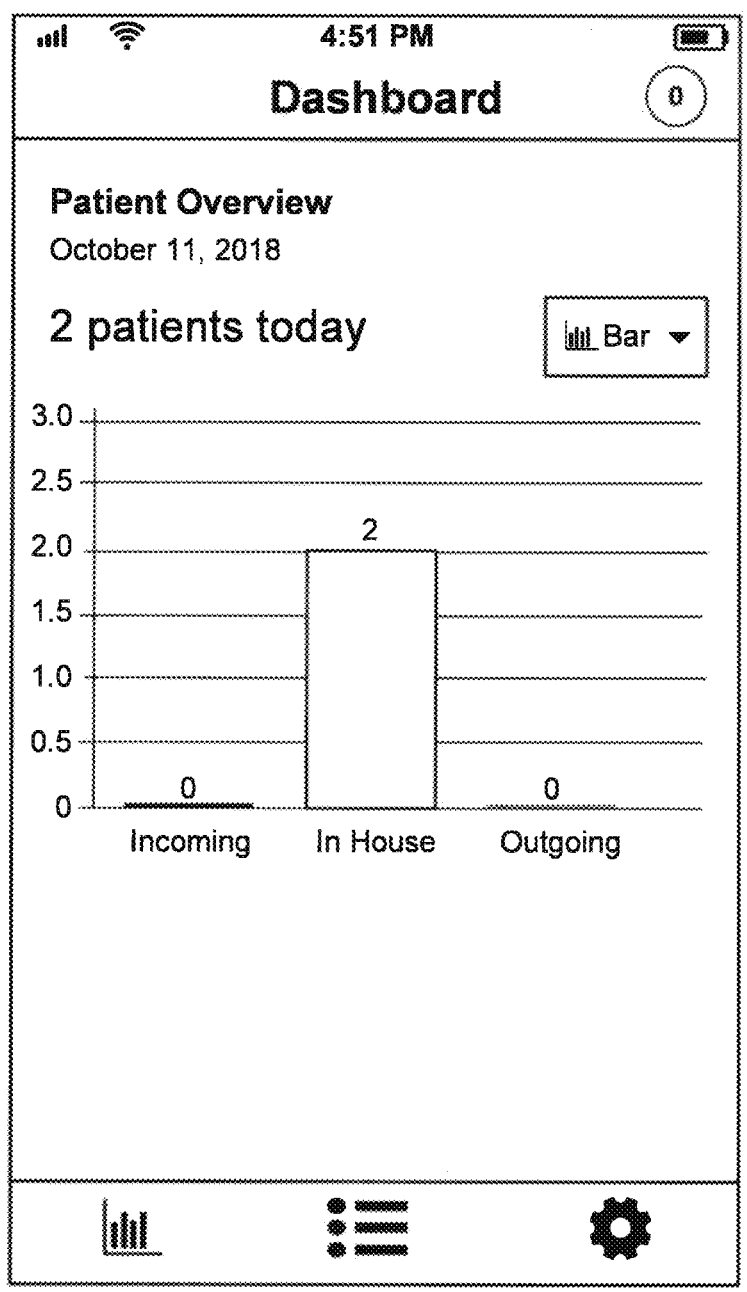
FIG. 13 is a twelfth example graphical user interface for visualizing data from a secure database pull in a role-based application, according to an example embodiment of the present disclosure.

FIG. 13 depicts a graphical user interface 1250 for visualizing data from a secure database pull in a role-based application, for example in a bed-side nurse role. Interface 1250 may be generated for display on a screen of a user interface device (e.g., screen 1601 of FIG. 23). In the example of FIG. 13, a patient flow manager is permitted to access display a patient overview of the number of incoming, in house, and outgoing patients.

Figure 14:
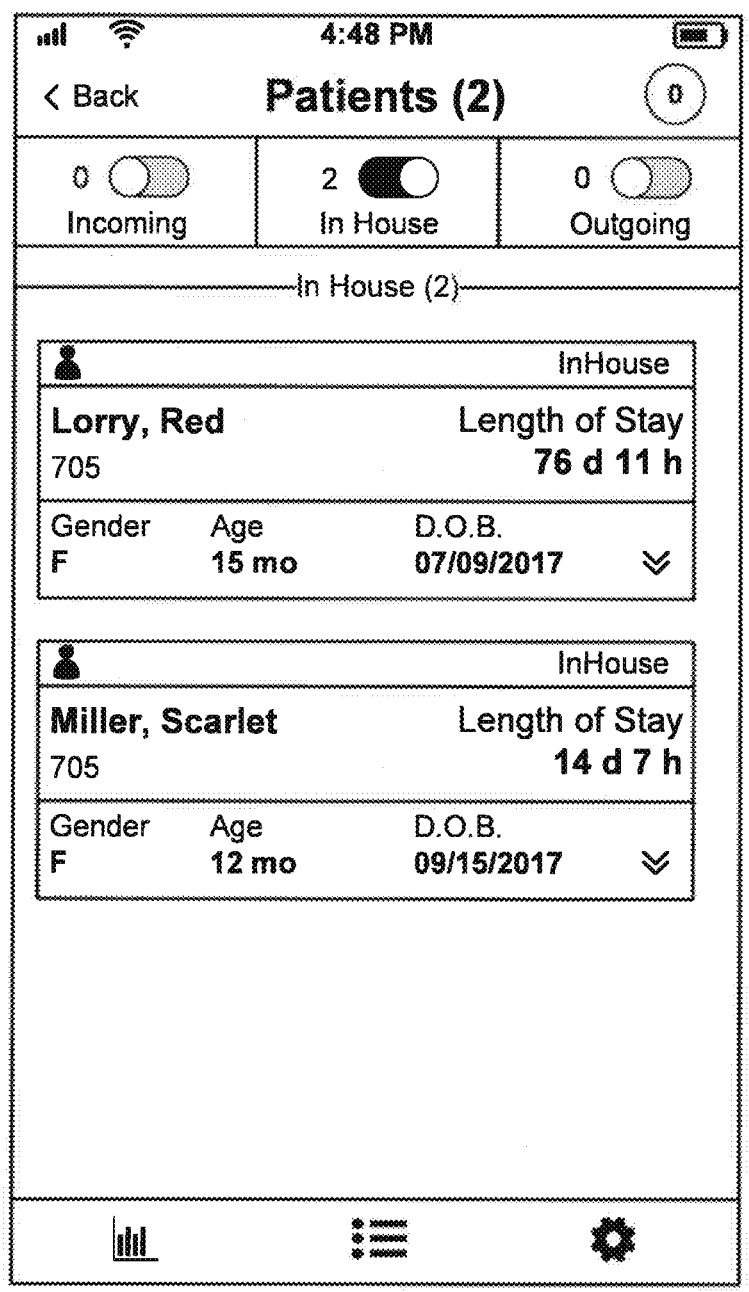
FIG. 14 is a thirteenth example graphical user interface for visualizing data from a secure database pull in a role-based application, according to an example embodiment of the present disclosure.

FIG. 14 depicts a graphical user interface 1400 for visualizing data from a secure database pull in a role-based application, for example in a bed-side nurse role. Interface 1400 may be generated for display on a screen of a user interface device (e.g., screen 1601 of FIG. 23). In the example of FIG. 14, a patient flow manager is permitted to access additional details on each patient from the list of patients, e.g., by opening a drop-down menu. The patient flow manager can adjust the viewing list between the incoming, in house, and outgoing patients.

Figure 15:
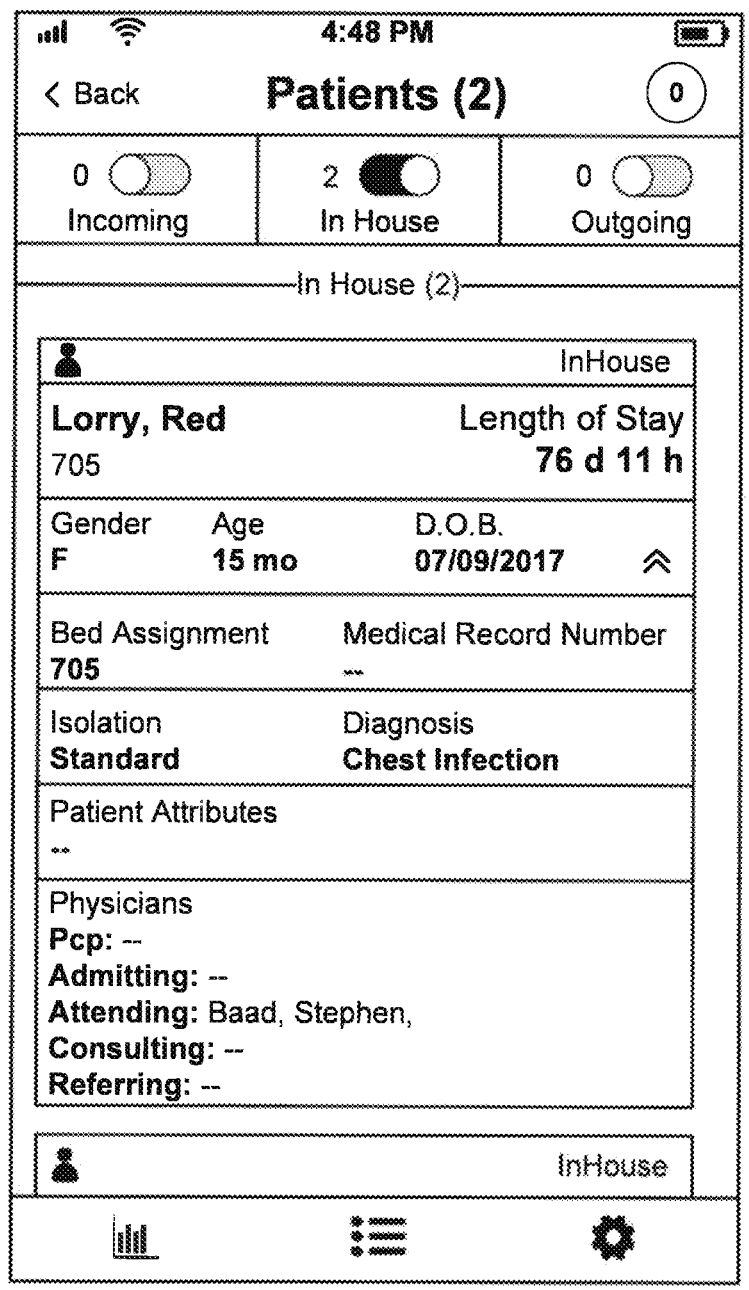
FIG. 15 is a fourteenth example graphical user interface for visualizing data from a secure database pull in a role-based application, according to an example embodiment of the present disclosure.

FIG. 15 depicts a graphical user interface 1450 for visualizing data from a secure database pull in a role-based application, for example in a bed-side nurse role. Interface 1450 may be generated for display on a screen of a user interface device (e.g., screen 1601 of FIG. 23). In the example of FIG. 15, a patient flow manager is permitted to access additional details on a specific patient from the list of patients, e.g., by clicking on the patient. The patient flow manager can adjust the viewing list between the incoming, in house, and outgoing patients.

Figure 16:
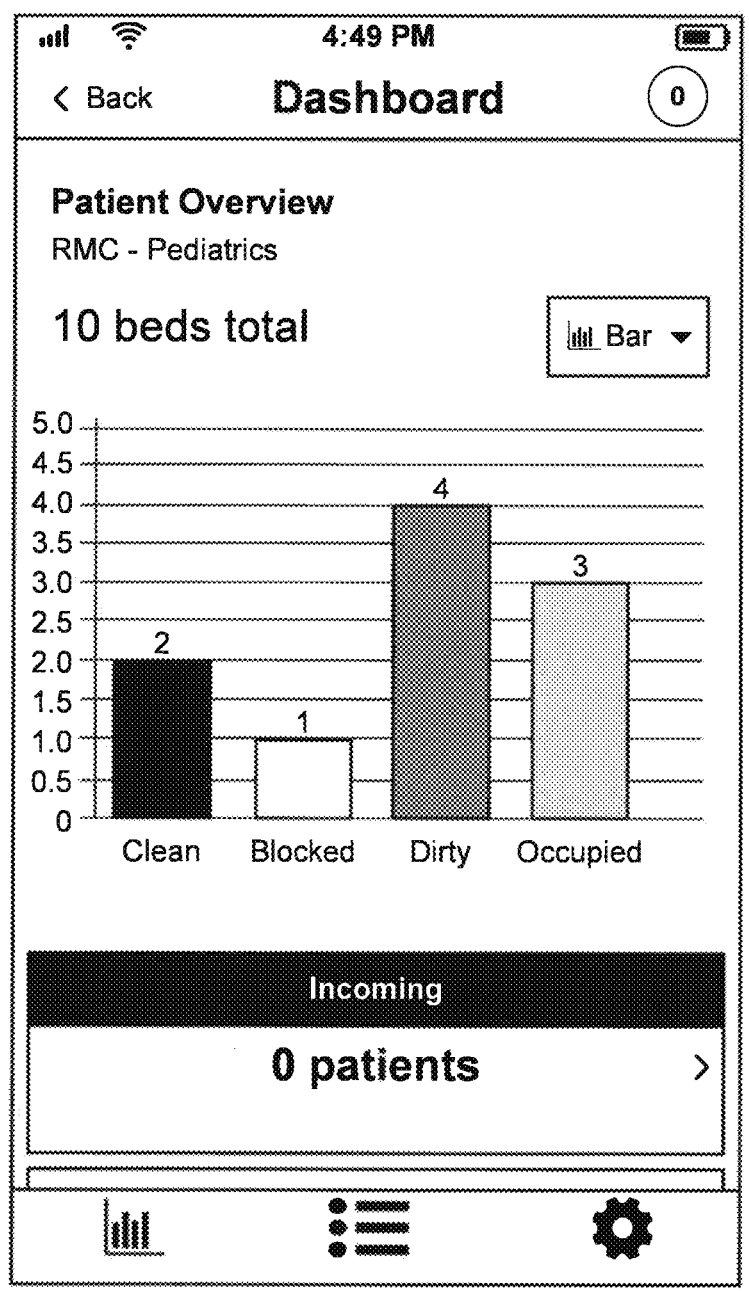
FIG. 16 is a fifteenth example graphical user interface for visualizing data from a secure database pull in a role-based application, according to an example embodiment of the present disclosure.

FIG. 16 depicts a graphical user interface 1550 for visualizing data from a secure database pull in a role-based application, for example in a charge nurse role. Interface 1550 may be generated for display on a screen of a user interface device (e.g., screen 1601 of FIG. 23). In the example of FIG. 16, a patient flow manager is permitted to access additional details on the total number of beds that are cleaned, blocked, dirty, and occupied as well as the number of incoming patients. Similar details may be accessed from unit-specific, bed-specific, or category-specific lists of patients or the like.

Figure 17:
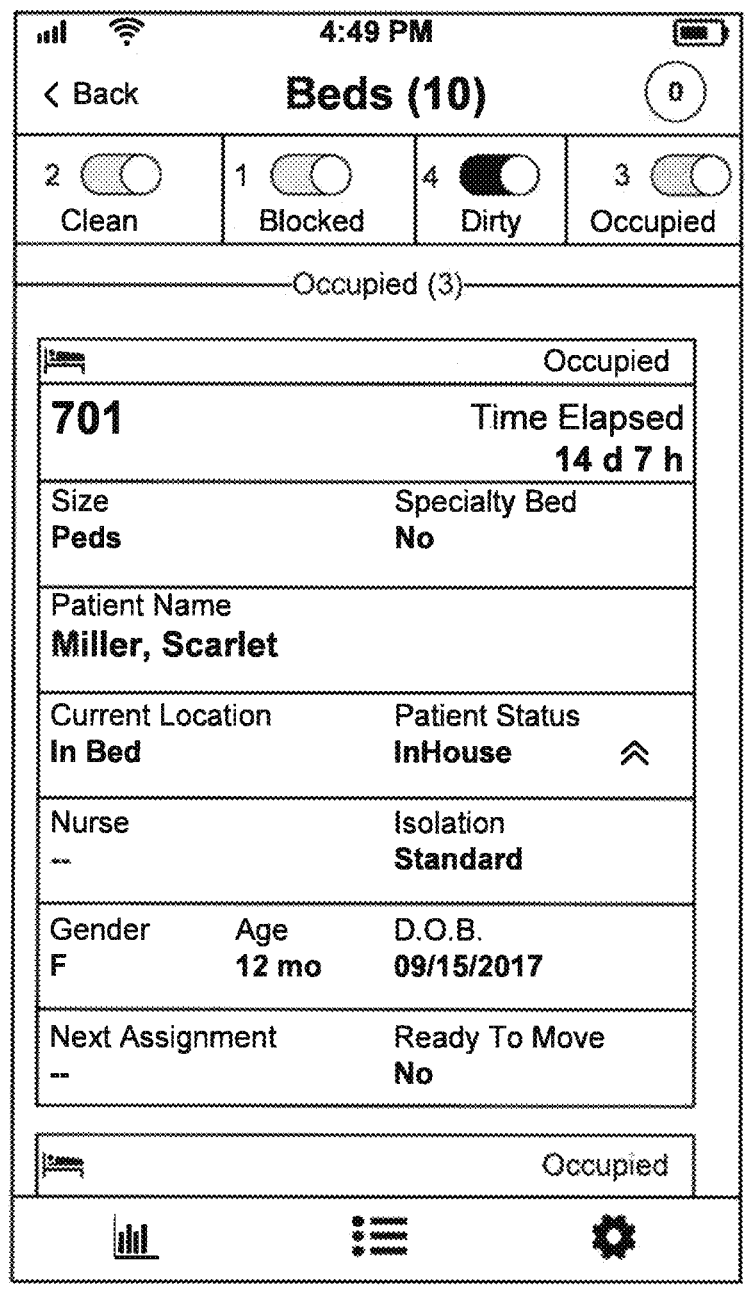
FIG. 17 is a sixteenth example graphical user interface for visualizing data from a secure database pull in a role-based application, according to an example embodiment of the present disclosure.

FIG. 17 depicts a graphical user interface 1700 for visualizing data from a secure database pull in a role-based application, for example in a charge nurse role. Interface 1700 may be generated for display on a screen of a user interface device (e.g., screen 1601 of FIG. 23). In the example of FIG. 17, a patient flow manager is permitted to access additional details on a specific bed from a list of beds e.g., by selecting the bed. Similar details may be accessed from unit-specific or category-specific lists of patients or the like.

Figure 18:
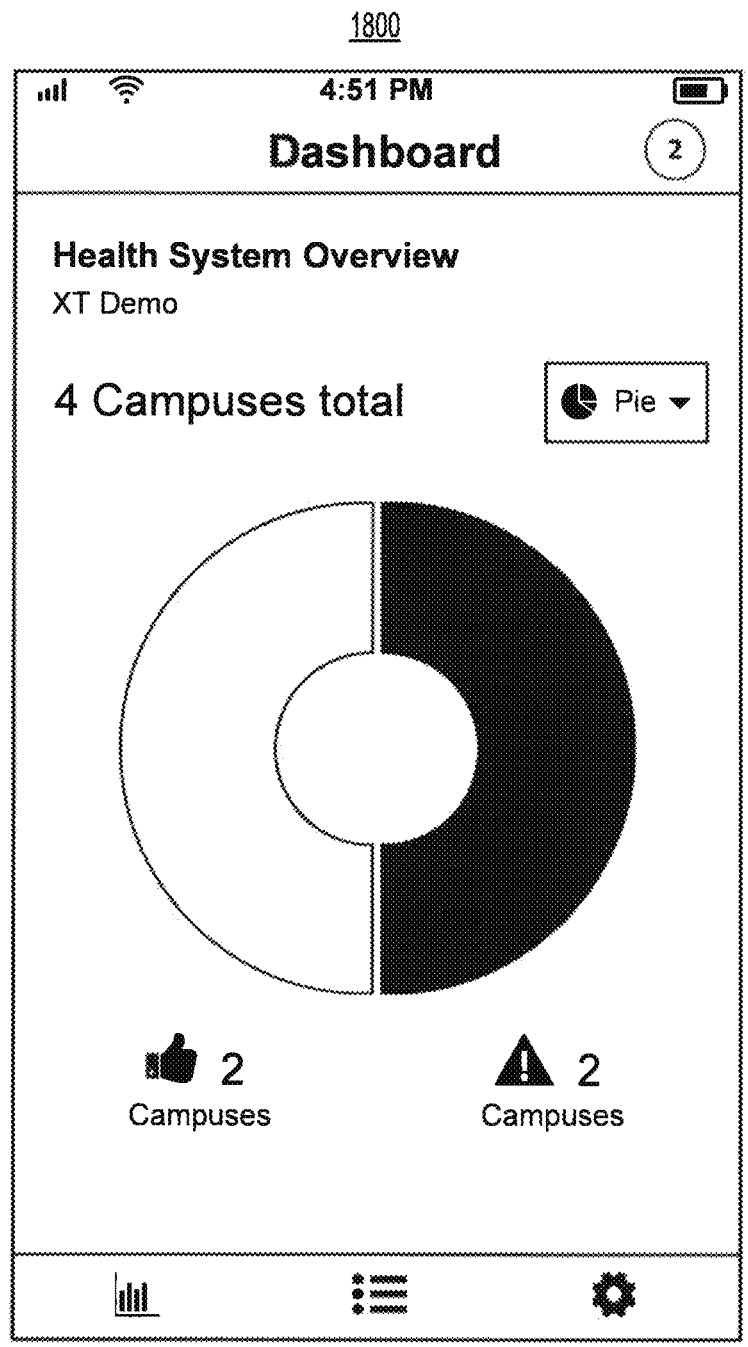
FIG. 18 is a seventeenth example graphical user interface for visualizing data from a secure database pull in a role-based application, according to an example embodiment of the present disclosure.

FIG. 18 depicts a graphical user interface 1800 for visualizing data from a secure database pull in a role-based application, for example in an executive nurse role. Interface 1800 may be generated for display on a screen of a user interface device (e.g., screen 1601 of FIG. 23). In the example of FIG. 18, a patient flow manager is permitted to access an overview of medical campuses indicating a status of the number of medical campuses. Similar details may be accessed from unit-specific or category-specific lists of patients or the like.

Figure 19:
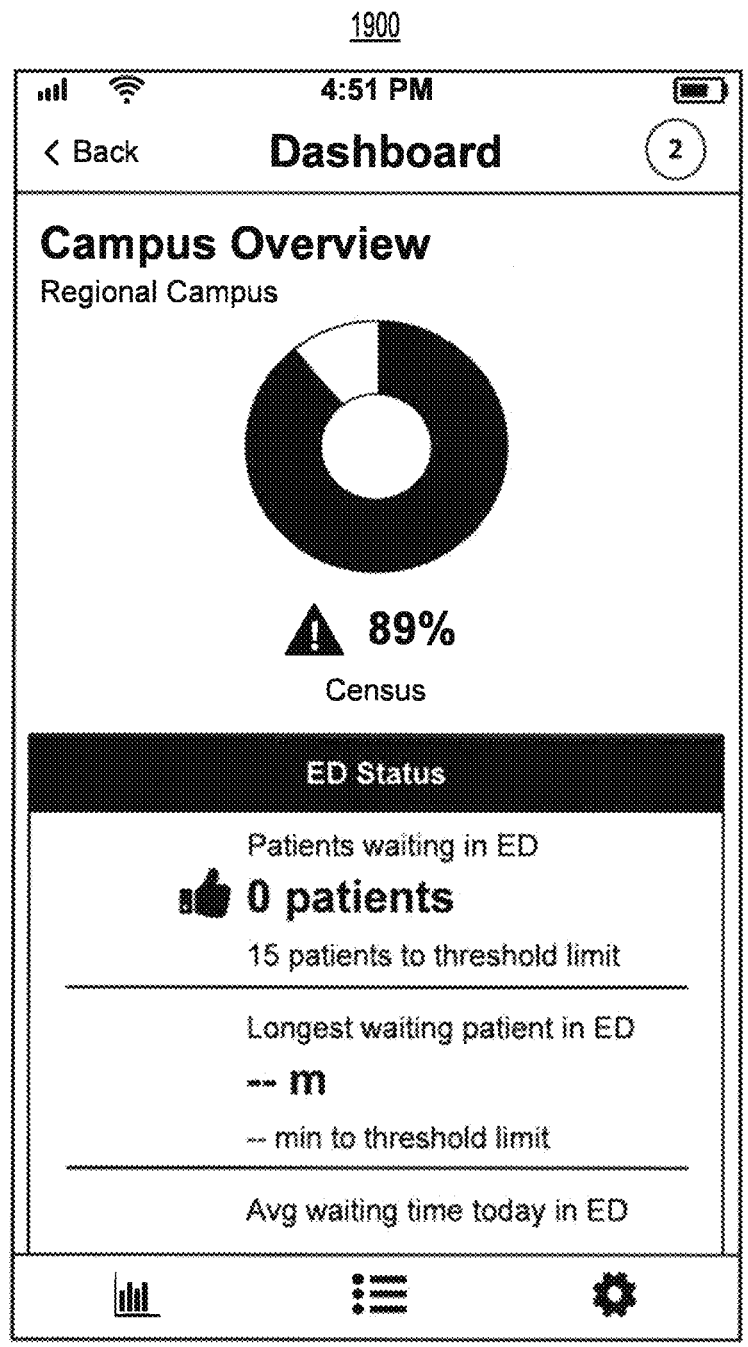
FIG. 19 is an eighteenth example graphical user interface for visualizing data from a secure database pull in a role-based application, according to an example embodiment of the present disclosure.

FIG. 19 depicts a graphical user interface 1900 for visualizing data from a secure database pull in a role-based application, for example in an executive nurse role. Interface 1900 may be generated for display on a screen of a user interface device (e.g., screen 1601 of FIG. 23). In the example of FIG. 19, a patient flow manager is permitted to access additional details on each campus indicating capacity metrics of that campus. Similar details may be accessed from unit-specific or category-specific lists of patients or the like.

Figure 20:
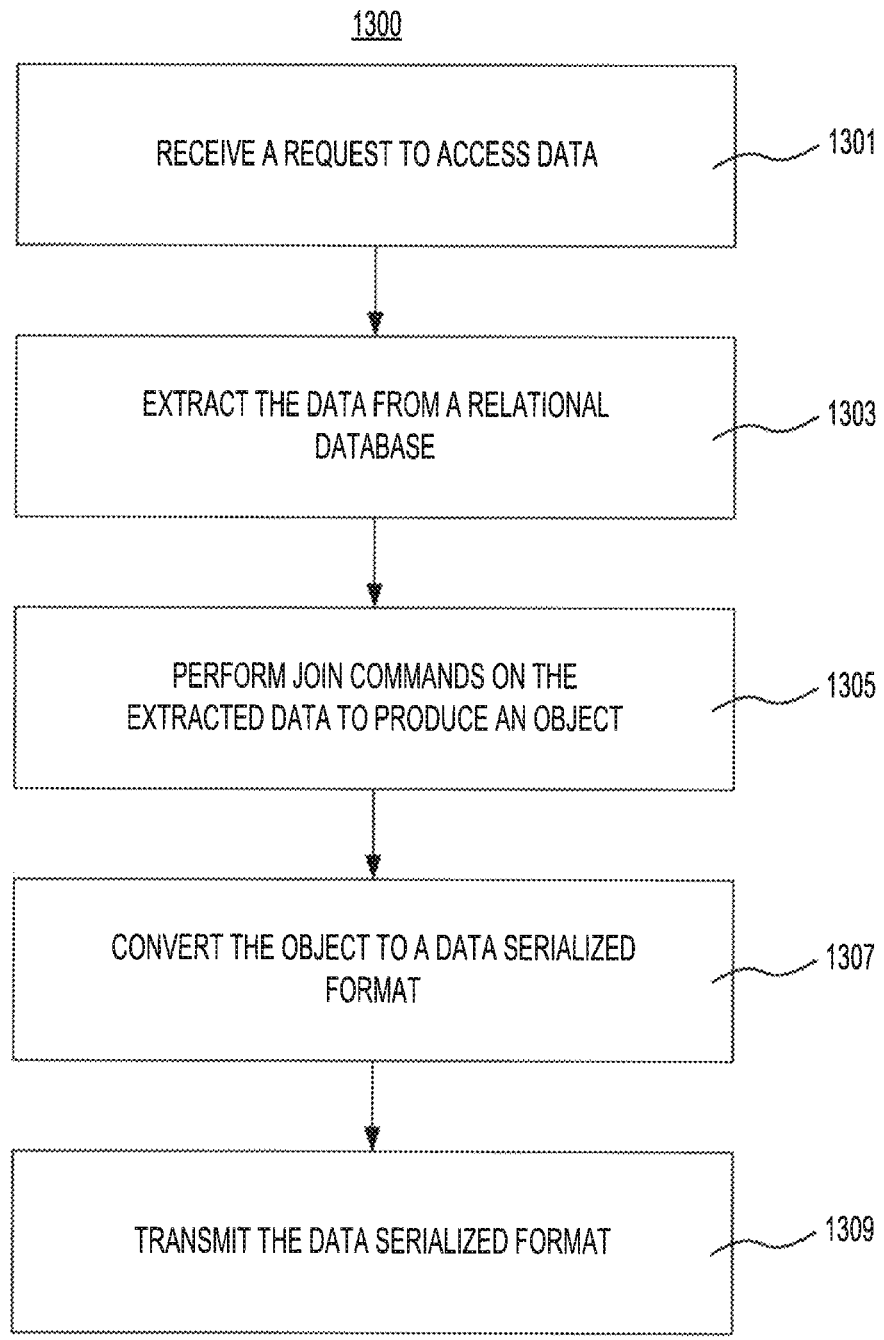
FIG. 20 is a flowchart of an example method for fulfilling secure database requests from a role-based application, according to an example embodiment of the present disclosure.

FIG. 20 depicts an example method 1300 for fulfilling secure database requests from a role-based application. Method 1300 may be implemented using one or more processors (e.g., processor 1503 of FIG. 22).

At step 1301, the processor may receive a request to access data from a relational database. For example, the user may comprise a caregiver (such as a doctor, nurse, surgeon, or the like) and may send the request using a user interface device. The request may be sent over one or more computer networks, such as the Internet, a local area network (LAN), or the like, and may be sent using WiFi, 4G, Ethernet, or the like. In some embodiments, to retain security, the request may be sent over a private network (such as a LAN) and/or may be encrypted (e.g., using an Advanced Encryption Standard (AES)). In embodiments where the request is encrypted, the processor may decrypt the request using a private key. In some embodiments, the request received from the user device may comprise an API pull of a data serialized format. In some embodiments, mobile servers may access a mobile store, the mobile store having a plurality of mobile applications that may store data. The mobile servers may transmit a query to the mobile store to aggregate the data from the mobile applications. The mobile servers may submit queries to the mobile store regularly (e.g. at two-minute intervals) in order to maintain a real-time access to the data.

The relational database may store data relating to patients in a hospital or other medical campus or network. For example, data may be stored and indexed based on patient and/or based on beds. In some embodiments, the processor may aggregate patient-specific and/or bed-specific data into one or more statistics, as explained above.

At step 1303, based on the request, the processor may extract the data from the relational database. For example, the servers may generate one or more commands in an appropriate relational database language such as SQL to extract the data. In embodiments where the aggregated data is stored as one or more objects, the servers may extract the aggregated data using an index or other matching technique to match the appropriate object(s) to the request. In some embodiments, the servers may perform one or more join commands on at least part of the extracted data (e.g., a part that is not already stored in an object) to generate an object in an object-oriented programming language having the joined data.

In some embodiments, at least a portion of the data in the database may be encrypted. In such embodiments, method 1300 may further include decrypting the data during extraction.

At step 1305, the processor may perform one or more join commands on the data to generate an object in an object-oriented programming language having the joined data. In some embodiments, as described above, step 1305 may be performed, at least in part, during aggregation of the data in the database. The processor may then perform one or more join commands on any extracted data not already converted to object(s).

At step 1307, the processor may convert the object to a data serialized format configured for use in a graphical user interface generator. For example, the objects may be converted to a JavaScript Object Notation (JSON) file, an Extensible Markup Language (XML) file, or the like. Such files may allow for compatibility with web-based APIs.

The data serialized format may be configured for use in a graphical user interface generator. For example, the graphical user interface generator may generate any of the graphical user interfaces described and depicted above.

At step 1309, the processor may transmit the data serialized format to the user device. For example, the servers may transmit the data serialized format over one or more computer networks, such as the Internet, a local area network (LAN), or the like, and may be sent using WiFi, 4G, Ethernet, or the like. In some embodiments, to retain security, the data serialized format may be sent over a private network (such as a LAN) and/or may be encrypted (e.g., using an Advanced Encryption Standard (AES)). In embodiments where the data serialized format is encrypted, the user interface device may decrypt the data serialized format, e.g., using a private key.

Method 1300 may include additional steps. For example, method 1300 may further include encrypting at least a portion of the data serialized format. For example, the portion may correspond to any portion of the data including patient-specific data (such as personal health information (PHI)).

By way of further example, the processor may monitor the aggregated data and transmit a notification to the user when a threshold is reached, as explained above. The threshold may be determined by the system or in accordance with one or more settings selected by the user.

Figure 21:
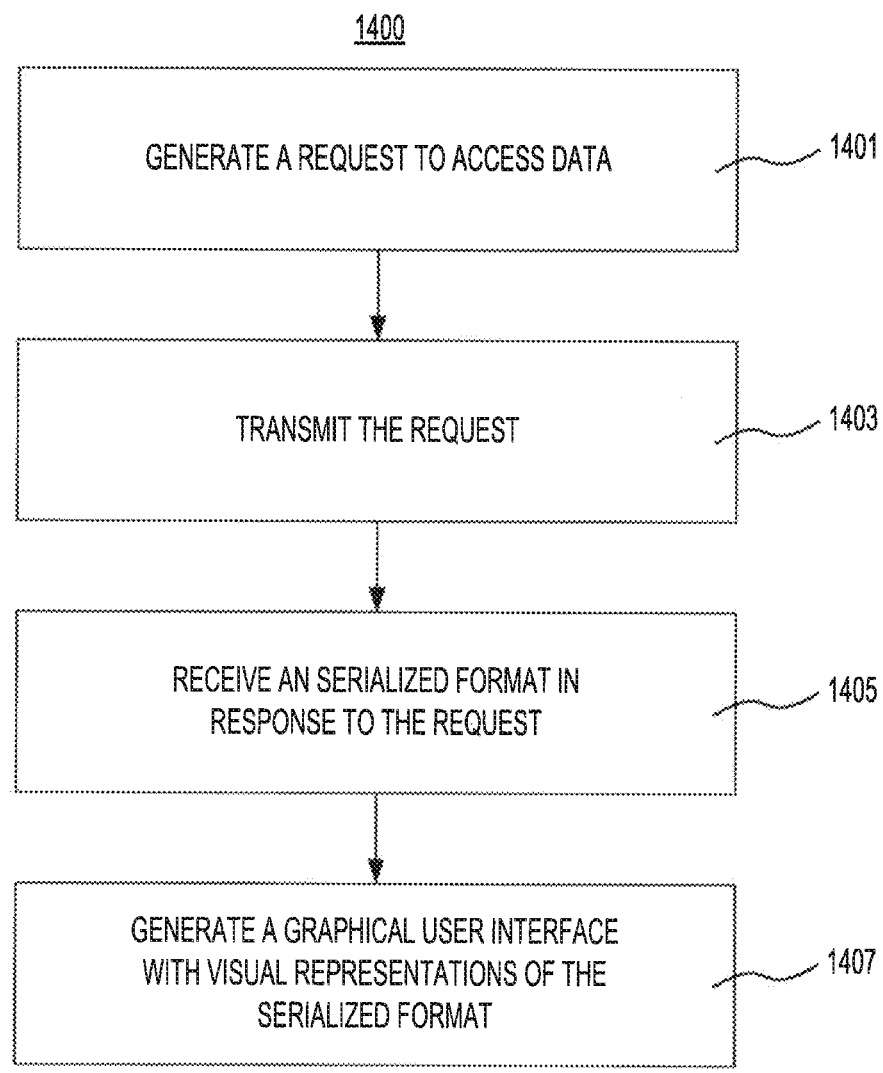
FIG. 21 is a flowchart of an example method for generating fulfilling secure database requests in a role-based application, according to an example embodiment of the present disclosure.

FIG. 21 depicts an example method 1400 for generating secure database requests in a role-based application. Method

Figure 23:
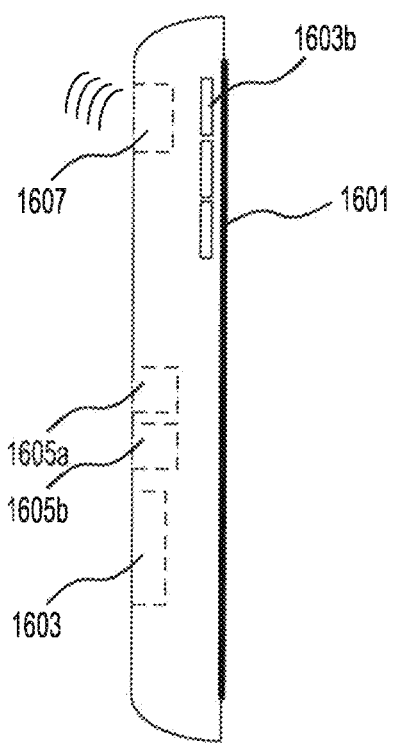
FIG. 23 is a block diagram of an example user interface device with which the systems, methods, and apparatuses of the present invention may be implemented.

1400 may be implemented using one or more processors (e.g., processor 1605 of FIG. 23).

At step 1401, the processor may generate a request for data from a relational database. The data requested may be selected selected based on user input and based on a role of the user, as explained above.

At step 1403, the processor may transmit the request to a remote device. For example, the user interface device may transmit the request over one or more computer networks, such as the Internet, a local area network (LAN), or the like, and may be sent using WiFi, 4G, Ethernet, or the like. In some embodiments, to retain security, the request may be sent over a private network (such as a LAN) and/or may be encrypted (e.g., using an Advanced Encryption Standard (AES)). In embodiments where the request is encrypted, the remote device may decrypt the request, e.g., using a private key.

At step 1405, the processor may receive, in response to the request, a data serialized format including the data. For example, the data serialized format may comprise a JavaScript Object Notation (JSON) file, an Extensible Markup Language (XML) file, or the like.

At step 1407, the processor may generate a graphical user interface including visual representations of the data in the data serialized format. For example, the customized graphical interfaces discussed above may be used to display the data. Graphical representations may include pie charts, bar graphs, and other visual representations of the received data. The graphical interfaces may also include text and numbers displaying the received data.

In some embodiments, the generated graphical user interface may be selected from a plurality of graphical user interfaces based on the requested data and based on the role. For example, the processor may select from one of the disclosed graphical interfaces (or variations thereof) based on the received data and based on the role. For example, the graphical interface will display data on a per-campus basis if the received data is organized on a per-campus basis. By way of further example, the level of detail extracted may depend on the role. In one example, per-bed details may be omitted if the role of the user is an executive. In another example, names of patients may be omitted if the role of the user is a nurse manager. In some embodiments, the graphical interface may be based on the role because the received data was previously based on the role and is used to select the graphical user interfaces.

Figure 22:
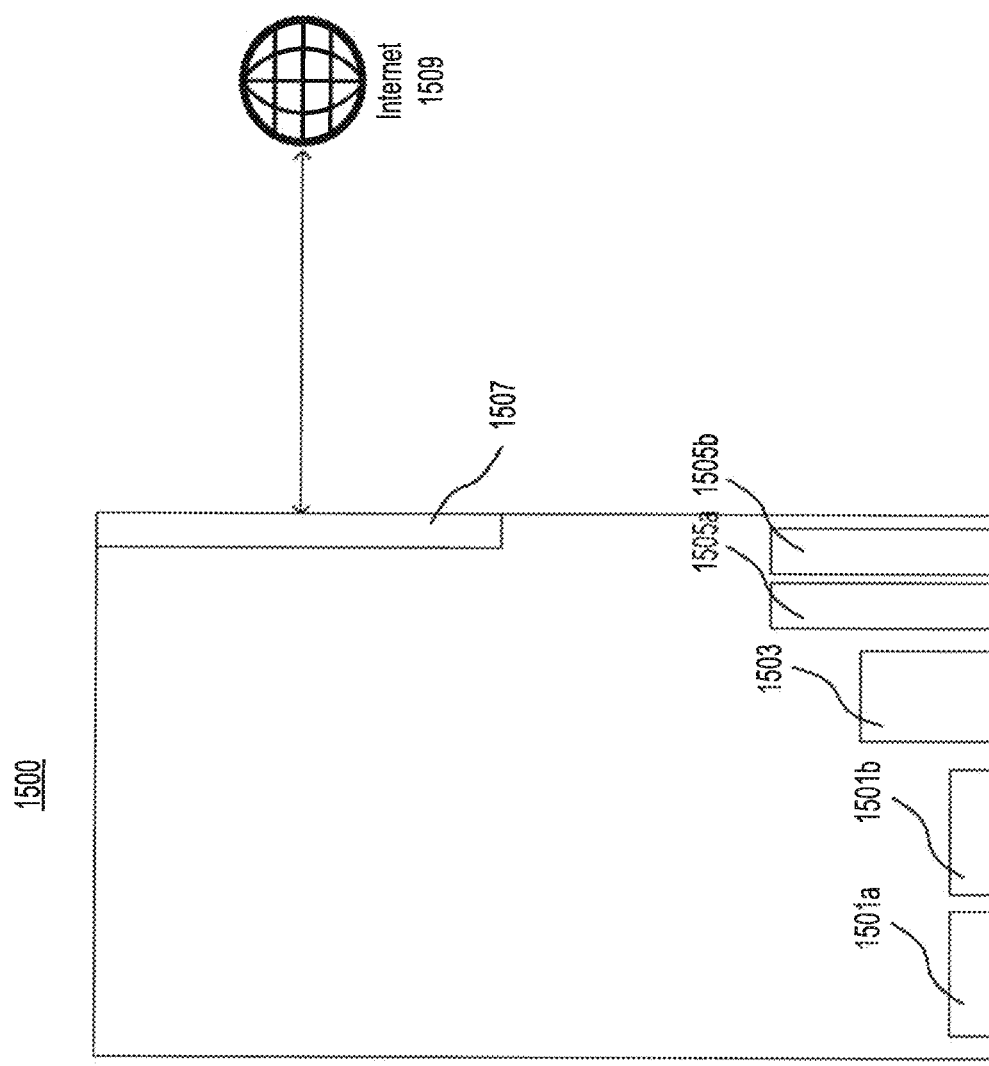
FIG. 22 is a block diagram of an example server with which the systems, methods, and apparatuses of the present invention may be implemented.

FIG. 22 is block diagram of an example device 1500 suitable for implementing the disclosed systems and methods. For example, device 1500 may execute method 1300 of FIG. 20. Device 1500 may comprise a server, desktop computer, or the like.

As depicted in FIG. 22, example server 1500 may include at least one processor (e.g., processor 1503) and at least one memory (e.g., memories 1505*a* and 1505*b*).

Processor 1503 may comprise a central processing unit (CPU), a graphics processing unit (GPU), or other similar circuitry capable of performing one or more operations on a data stream. Processor 1503 may be configured to execute instructions that may, for example, be stored on one or more of memories 1505*a* and 1505*b*.

Memories 1505*a* and 1505*b* may be volatile memory (such as RAM or the like) and/or non-volatile memory (such as flash memory, a hard disk drive, or the like). As explained above, memories 1505*a* and 1505*b* may store instructions for execution by processor 1503.

As further depicted in FIG. 22, server 1500 may include at least one network interface controller (NIC) (e.g., NIC 1507). NIC 1507 may be configured to facilitate communication over at least one computing network (e.g., network 1509, which is depicted in the example of FIG. 22 as the Internet). Communication functions may thus be facilitated through one or more NICs, which may be wireless and/or wired and may include an Ethernet port, radio frequency receivers and transmitters, and/or optical (e.g., infrared) receivers and transmitters. The specific design and implementation of the one or more NICs depend on the computing network 1509 over which server 1500 is intended to operate. For example, in some embodiments, server 1500 may include one or more wireless and/or wired NICs designed to operate over a GSM network, a GPRS network, an EDGE network, a Wi-Fi or WiMax network, and a Bluetooth® network. Alternatively or concurrently, server 1500 may include one or more wireless and/or wired NICs designed to operate over a TCP/IP network.

As depicted in FIG. 22, server 1500 may include and/or be operably connected to one or more storage devices, e.g., storages 1501*a* and 1501*b*. Storage devices 1501*a* and 1501*b* may be volatile (such as RAM or the like) or non-volatile (such as flash memory, a hard disk drive, or the like).

Processor 1503, memories 1505*a* and 1505*b*, NIC 1507, and/or storage devices 1501*a* and 1501*b* may comprise separate components or may be integrated in one or more integrated circuits. The various components in server 1500 may be coupled by one or more communication buses or signal lines (not shown).

FIG. 23 is block diagram of an example user interface device for implementing the disclosed systems and methods. Device 1600 may comprise a smartphone, tablet, or the like.

Device 1600 may have a screen 1601. For example, screen 1601 may display one or more graphical user interfaces (e.g., interfaces 200-1200 of FIGS. 2-12) that visualize data from a secure database pull in a role-based application. In certain aspects, screen 1601 may comprise a touchscreen to facilitate use of the one or more GUIs.

As further depicted in FIG. 23, device 1600 may have at least one processor 1603. For example, at least one processor 1603 may comprise a system-on-a-chip (SOC) adapted for use in a portable device, such as device 1600. Alternatively or concurrently, at least one processor 1603 may comprise any other type(s) of processor.

As further depicted in FIG. 23, device 1600 may have one or more memories, e.g., memories 1605*a* and 1605*b*. In certain aspects, some of the one or more memories, e.g., memory 1605*a*, may comprise a volatile memory. In such aspects, memory 1605*a*, for example, may store one or more applications (or "apps") for execution on at least one processor 1603. For example, an app may include an operating system for device 1600 and/or an app for executing method 1400 of FIG. 21. In addition, memory 1605*a* may store data generated by, associated with, or otherwise unrelated to an app in memory 1605*a*.

Alternatively or concurrently, some of the one or more memories, e.g., memory 1605*b*, may comprise a non-volatile memory. In such aspects, memory 1605*b*, for example, may store one or more applications (or "apps") for execution on at least one processor 1603. For example, as discussed above, an app may include an operating system for device 1600 and/or an app for executing method 1400 of FIG. 21. In addition, memory 1605*b* may store data generated by, associated with, or otherwise unrelated to an app in memory 1605*b*. Furthermore, memory 1605*b* may include a pagefile, swap partition, or other allocation of storage to allow for the use of memory 1605b as a substitute for a volatile memory if, for example, memory 1605a is full or nearing capacity.

As depicted in FIG. 23, device 1600 may include at least one network interface controller (NIC) (e.g., NIC 1607). NIC 1607 may be configured to facilitate communication over at least one computing network. Communication functions may thus be facilitated through one or more NICs. Although depicted in wireless in FIG. 23 and including radio frequency receivers and transmitters and/or optical (e.g., infrared) receivers and transmitters, NIC 1607 may alternatively be wired and include an Ethernet port or the like. The specific design and implementation of the one or more NICs depend on the computing network over which user interface device 1600 is intended to operate. For example, in some embodiments, user interface device 1600 may include one or more wireless and/or wired NICs designed to operate over a GSM network, a GPRS network, an EDGE network, a Wi-Fi or WiMax network, and a Bluetooth® network. Alternatively or concurrently, user interface device 1600 may include one or more wireless and/or wired NICs designed to operate over a TCP/IP network.

Each of the above identified instructions and applications may correspond to a set of instructions for performing one or more functions described above. These instructions need not be implemented as separate software programs, procedures, or modules. Disclosed memories may include additional instructions or fewer instructions. Furthermore, various functions of server 1500 and/or user interface device 1600 may be implemented in hardware and/or in software, including in one or more signal processing and/or application specific integrated circuits.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented with hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive.

Instructions or operational steps stored by a computer-readable medium may be in the form of computer programs, program modules, or codes. As described herein, computer programs, program modules, and code based on the written description of this specification, such as those used by the processor, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A system for fulfilling secure database requests from a role-based application, the system comprising:
   at least one memory storing instructions; and
   at least one processor configured to execute the instructions to:
   receive, from a user device, a request comprising an application program interface (API) pull of a data in a data serialized format from a relational database, wherein the request is generated automatically based upon user navigation within an application, wherein the relational database comprises data associated with a health facility;
   based on the request, extract the data from the relational database;
   perform one or more join commands on the data to generate an object in an object-oriented programming language, the generated object having the joined data;
   convert the object to the data serialized format configured for use in a graphical user interface generator of the user device; and
   transmit the data serialized format to the user device.

2. The system of claim 1 wherein:
   the relational database is in communication with a mobile store, the mobile store having a plurality of mobile applications that store and receive data.

3. The system of claim 2 wherein:
   the request to access data is transmitted to the mobile store.

4. The system of claim 2 wherein:
   the request to access data is transmitted to the mobile store and data stored on the plurality of mobile applications is aggregated based on the request.

5. The system of claim 1 wherein:
   the request to access data is transmitted at regular intervals to maintain a real-time access to the data.

6. The system of claim 1, the data comprising:
   a total number of available beds, a total number of occupied beds, and a total number of patients.

7. The system of claim 1, the data comprising:
   a percentage of available beds, a percentage of patients awaiting care, and a percentage of patients receiving care.

8. The system of claim 1, the data comprising:
a percentage of vacant beds, a percentage of vacant beds that are clean, and a percentage of vacant beds that are dirty.

9. A non-transitory, computer-readable medium storing instructions for generating secure database requests in a role-based application, the instructions causing one or more processors to:
generate a request comprising an application program interface (API) pull of data in a data serialized format from a relational database, wherein the request is generated automatically based upon user navigation within an application, wherein the relational database comprises data associated with a health facility;
transmit the request to a remote device;
receive, in response to the request, the data in a data serialized format including the data; and
generate a graphical user interface comprising visual representations of the data in the data serialized format, wherein:
the data requested is selected based on user input and based on a role of the user, and
the generated graphical user interface is selected from a plurality of graphical user interfaces based on the requested data and based on the role.

10. The computer readable medium of claim 9 wherein:
the relational database is in communication with a mobile store, the mobile store having a plurality of mobile applications that store and receive data.

11. The computer readable medium of claim 10 wherein:
the request to access data is transmitted to the mobile store.

12. The computer readable medium of claim 10 wherein:
the request to access data is transmitted to the mobile store and data stored on the plurality of mobile applications is aggregated based on the request.

13. The computer readable medium of claim 9 wherein:
the request to access data is transmitted at regular intervals to maintain a real-time access to the data.

14. The computer readable medium of claim 9, the data comprising:
a total number of available beds, a total number of occupied beds, and a total number of patients.

15. The computer readable medium of claim 9, the data comprising:
a percentage of available beds, a percentage of patients awaiting care, and a percentage of patients receiving care.

16. The computer readable medium of claim 9, the data comprising:
a percentage of vacant beds, a percentage of vacant beds that are clean, and a percentage of vacant beds that are dirty.

17. A computer implemented method for generating secure database requests in a role-based application, the method comprising:
receiving, from a user device, a request comprising an application program interface (API) pull of a data in a data serialized format from a relational database, wherein the request is generated automatically based upon user navigation within an application, wherein the relational database comprises data associated with a health facility;
extracting the data from the relational database based on the request;
performing one or more join commands on the data to generate an object in an object-oriented programming language, the generated object having the joined data;
converting the object to a data serialized format configured for use in a graphical user interface generator of the user device; and
transmitting the data serialized format to the user device.

18. The computer implemented method of claim 17 wherein:
the relational database is in communication with a mobile store, the mobile store having a plurality of mobile applications that store and receive data.

19. The computer implemented method of claim 18 wherein:
the request to access data is transmitted to the mobile store.

20. The computer implemented method of claim 18 wherein:
the request to access data is transmitted to the mobile store and data stored on the plurality of mobile applications is aggregated based on the request.

\* \* \* \* \*